(12) United States Patent
Fine et al.

(10) Patent No.: US 6,852,760 B1
(45) Date of Patent: Feb. 8, 2005

US006852760B1

(54) COMPOSITIONS AND METHODS FOR TREATMENT FOR GLUCOSE METABOLISM DISORDERS

(75) Inventors: Stuart A. Fine, Northbrook, IL (US); Kevin J. Kinsella, La Jolla, CA (US)

(73) Assignee: Akesis Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/787,325

(22) PCT Filed: Sep. 17, 1999

(86) PCT No.: PCT/US99/21377

§ 371 (c)(1),
(2), (4) Date: Jun. 4, 2001

(87) PCT Pub. No.: WO00/15211

PCT Pub. Date: Mar. 23, 2000

Related U.S. Application Data

(63) Continuation-in-part of application No. 09/156,102, filed on Sep. 17, 1998, now Pat. No. 6,376,549.
(60) Provisional application No. 60/126,489, filed on Mar. 26, 1999.

(51) Int. Cl.[7] .................. A61K 31/175; A61K 31/17; A61K 33/26; A61K 33/24
(52) U.S. Cl. .................. 514/593; 514/594; 514/595; 514/596; 424/646; 424/655
(58) Field of Search ................ 514/186, 593, 514/594, 595, 596; 424/646, 655

(56) References Cited

U.S. PATENT DOCUMENTS

| | | | |
|---|---|---|---|
| 4,921,877 A | 5/1990 | Cashmere et al. | 514/866 |
| 4,959,222 A | 9/1990 | Nadland et al. | 424/692 |
| 5,013,752 A | 5/1991 | Dobbins | 514/505 |
| 5,045,316 A | 9/1991 | Kaplan | 424/400 |
| 5,069,913 A | 12/1991 | Posner et al. | 424/646 |
| 5,087,623 A | 2/1992 | Boynton et al. | 514/188 |
| 5,087,624 A | 2/1992 | Boynton et al. | 514/188 |
| RE33,988 E | 7/1992 | Evans | 614/188 |
| 5,164,384 A | 11/1992 | Paul | 514/188 |
| 5,215,750 A | 6/1993 | Keane, II | 424/440 |
| 5,266,560 A | 11/1993 | Furman et al. | 514/4 |
| 5,300,496 A | 4/1994 | McNeill et al. | 514/184 |
| 5,308,627 A | 5/1994 | Umbdenstock, Jr. | 424/639 |
| 5,332,579 A | 7/1994 | Umbdenstock | 424/639 |
| 5,496,827 A | 3/1996 | Patrick | 514/310 |
| 5,527,790 A | 6/1996 | McNeill et al. | 514/186 |
| 5,532,269 A | 7/1996 | Koltringer | 514/440 |
| 5,543,405 A | 8/1996 | Keown | 514/188 |
| 5,550,113 A | 8/1996 | Mann | 514/54 |
| 5,597,585 A | 1/1997 | Williams et al. | 424/579 |
| 5,599,835 A | 2/1997 | Fisher | 514/440 |
| 5,614,224 A | 3/1997 | Womack | 424/646 |
| 5,620,967 A | 4/1997 | McNeill et al. | 514/186 |
| 5,635,535 A | 6/1997 | Wagstaff | 514/557 |
| 5,637,324 A | 6/1997 | Bland | 424/655 |
| 5,641,531 A | 6/1997 | Liebrecht et al. | 426/583 |
| 5,654,011 A | 8/1997 | Jackson et al. | 424/635 |
| 5,665,385 A | 9/1997 | Johnson et al. | 424/451 |
| 5,707,980 A | 1/1998 | Knutson et al. | 514/167 |
| 5,730,988 A | 3/1998 | Womack | 424/195.1 |
| 5,763,484 A | 6/1998 | Horrobin | 514/560 |
| 5,770,215 A | 6/1998 | Moshyedi | 424/440 |
| 5,789,401 A | 8/1998 | McCarty | 514/188 |
| 5,807,586 A | 9/1998 | Jackson et al. | 424/630 |
| 5,817,329 A | 10/1998 | Gardiner | 424/439 |
| 5,849,338 A | 12/1998 | Richardson et al. | 424/682 |
| 5,866,563 A | 2/1999 | McNeil et al. | 514/186 |
| 5,871,769 A | 2/1999 | Fleming et al. | 424/423 |
| 5,885,980 A * | 3/1999 | Gutierrez et al. | 514/186 |
| 5,905,075 A | 5/1999 | Harpe et al. | 514/188 |
| 5,908,647 A | 6/1999 | Golightly et al. | 426/74 |
| 5,962,030 A | 10/1999 | Fine | 424/646 |
| 5,980,905 A | 11/1999 | De La Harpe et al. | 424/195.1 |
| 6,203,819 B1 | 3/2001 | Fine | 424/646 |
| 6,376,549 B1 | 4/2002 | Fine et al. | 514/635 |

FOREIGN PATENT DOCUMENTS

| | | |
|---|---|---|
| DE | 298 05 782 | 9/1998 |
| EP | 561 744 A1 | 9/1993 |
| EP | 0 834 318 A1 | 4/1998 |
| WO | WO 91/11117 | 8/1991 |
| WO | WO 96/25939 | 8/1996 |
| WO | WO 96/35421 | 11/1996 |
| WO | WO 96/39871 | 12/1996 |
| WO | WO 97/11614 | 4/1997 |
| WO | WO 98/04248 | 2/1998 |
| WO | WO 98/41113 | 9/1998 |
| WO | WO 98/42211 | 10/1998 |
| WO | WO 99/07387 | 2/1999 |
| WO | WO 00/12095 | 3/2000 |

OTHER PUBLICATIONS

Abbott et al., "The Impact of Diabetes on Survival Following Myocardial Infarction in Men vs Women," JAMA, 260(23):3456–3460 (1988).

ACC/AHA Task Force Report, "Guidelines for the Early Management of Patients with Acute Myocardial Infarction; a Report of the American College of Cardiology/ American Heart Association Task Force on Assessment of Diagnostic and Therapeutic Cardiovascualr Procedures (Subcommittee to Develop Guidelines for the Early Management of Patients with Acute Myocardial Infarction)," JACC, 16(2):249–292 (1990).

Aharon et al., "Vanadul Sulfate Does Not Enhance Insulin Action in Patients with Type I Diabetes," Diabetes Care, 21:2194–2195 (1998).

(List continued on next page.)

*Primary Examiner*—Theodore J. Criares
(74) *Attorney, Agent, or Firm*—Dana M. Gordon; Foley Hoag LLP

(57) ABSTRACT

Compositions and methods of using the same for the treatment of diabetes and other disorders of glucose metabolism are provided. Compositions may include an anti-diabetic agent and one or more of a bioavailable source of chromium and vanadium.

38 Claims, No Drawings

OTHER PUBLICATIONS

American Diabetes Association: "Nutrition Recommendations and Principles for People with Diabetes Mellitus," Diabetes Care, 19(1):S16–S19 (1996).

American Diabetes Association: "Nutrition Recommendations and Principles for People with Diabetes Mellitus," DiabetesCare, 20(1):S14–S17 (1997).

Amoikon, et al., "Effect of chromium tripicolinate on growth, glucose tolerance, insulin sensitivity, plasma metabolites, and growth hormone in pigs," J. Anim. Sic. (1995) 73(4) 1123–30 XP000901969 Abstract.

Anderson and Kozlovsky, "Chromium Intake, Absorption and Execretion of Subjects Consuming Self–Selected Diets," The American Journal of Clinical Nutrition, 41:1177–1183 (1985).

Anderson et al., "Elevated Intakes of Supplemental Chromium Improve Glucose and Insulin Varibles in Individuals With Type 2 Diabetes", Diabetes 46:1786–1791 (1997).

Anderson et al., Urinary Chromium Execretion and Insulinogenic Properties of Carbohydrates,: Am J Clin Nutr, 51:864–868 (1990).

Anderson, Richard "Chromium, Glucose Intolerance and Diabetes," The American Journal of Clinical Nutrition, vol. 17, No. 6 548–555 (1998).

Antiplatelet Trialists' Collaboration, "Collaborative overview of randomized trials of antiplatelet therapy–I: Prevention of death, myocardial infarction, and stroke by prolonged antiplatelet therapy in various categories of patients," BMJ 308:81–106 (1994).

Arsenian, M.A., "Magnesium and Cardiovascular Disease," Progress in Cardiovascular Disease 35(4):271–310 (1993).

Arsenian, M.A., "Magnesium and Autonomic Nervous System, " Magnesium and Cardiovascular Disease 291–310 (1993).

Avins, "Lowering Risk without Lowering Cholesteral: Implications of National Cholesterol Policy" Annals of Internal Medicine 125 (6):502–506 (1996).

Bailey, C.J., "Biguanides and NIDDM" Diabetes Care 15 (6):755–772 (1992).

Barnard, et al., "Diet and Exercise in Treatment of NIDDM; The need for early emphasis" Diabetes Care 17 (12):1469–1472 (1994).

Bayraktar, M., "A Comparison of Acarbose Versus Metformin as an Adjuvant Therapy in Sulfonylurea–Treated NIDDM Patients" Diabetes Care 19 (3):252–254 (1996).

Bierman, E.L., "Atherogenesis in diabetes" Arteriosclerosis and Thrombosis 12 (6):647–656 (1992).

Bloomgarden, A.T., "American Diabetes Association Scientific Sessions, 1995; Magnesium Deficiency, Atherosclerosis, and Health Care" Diabetes Care 18 (12):1623–1627 (1995).

Boyd et al., "Combined dietary chromium picolinate supplementation and an exercise program leads to a reduction of serum cholesterol and insulin in college–aged subjects," J. Nutr. Biochem. (1998) 9(8), 471–475 XP000901922 Abstract.

Caballero, "Vitamin E Improves the Action of Insulin" Nutrition Reviews 51 (11):339–340 (1993).

Calle–Pascual, A.L., "Comparison Between Acarbose, Metformin, and Insulin Treatment in Type 2 Diabetic Patients with Secondary Failure to Sulfonylurea Treatment" Diabete & Metabolisme (Paris) 21:256–260 (1995).

Cam et al., "Long—term effectiveness of oral vanadyl sulphate in streptozotocin–diabetic rats", Diabetologia 36: 218–224 (1993).

Cefalu, et al, "Effect of Chromium Picolinate on Insulin Sensitivity In Vivo", The Journal of Trace Elements in Experimental Medicine 12:71–83 (1999).

Cerulli et al., "Chromium Picolinate Toxicity", The Annals of Pharmacotherapy 32:428–431, ( Apr. 1998).

Cheng, et al, "Follow–up Survey of People in China with Type 2 Diabetes Mellitus Consuming Supplemental Chromium," The Journal of Trace Elements in Experimental Medicine 12:55–60 (1999).

Chowdhury and Lasker, "Elevated glycated haemoglobin in non–diabetic patients is associated with an increased mortality in myocardial infarction", Postgrad. Med. J. 74: 480–481 (1998).

Clarke, R. J., "Suppression of Thromboxane $A_2$ but not of Systemic Prostacyclin by Controlled–Release Aspirin" The New England Journal of Medicine 325 (16):1137–1141 (1991).

Classen, H. G., "Magnesium and Potassium Deprivation and Supplementation in Animals and Man: Aspects in View of Intestinal Absorption" Magnesium 3:257–264 (1984).

Cohen and Kitzes, "Magnesium Sulfate and Digitalis–Toxic Arrhythmias" JAMA 249 (20):2808–2810 (1983).

Cohen, et al., Oral Vanadyl Sulfate Improves Hepatic and Peripheral Insulin Sensitivity in Patients with Non–Insulin–dependent Diabetes Mellitus J. Clin. Invest. 95:2501–2509 (1995).

Colwell et al., "Correlation of Platelet Aggretation, Plasma Factor Activity, and Megathrombocytes in Diabetic Subjects With and Without Vascular Disease" Metabolism 26 (3):279–285 (1977).

Dai et al., "One–year Treatment of Streptozotocin–Induced Diabetic Rats with Vanadyl Sulphate" Pharmacology & Toxicology 74:101–109 (1994).

Davi et al., "Thromboxane $B_2$ Formation and Platelet Sensitivity to Prostacyclin in Insulin–Dependent and Insulin–Independent Diabetics" Thrombosis Research 26:359–370 (1982).

Davi et al., "Thromboxane Biosynthesis and Platelet Function in Type II Diabetes Mellitus" The New England Journal of Medicine 322 (25):1769–1774 (1990).

Davies et al., "Intramiocardial Platelet Aggregation in Patients with unstable Angina Suffering Sudden Ischemic Cardiac Death " Cirulation 73 (3):418–427 (1986).

Davis et al., "Monotherapy with Magnesium Increases Abnormally Low High Density Lipoprotein Cholesterol: A Clinical Assay" Current Therapeutic Research 36 (2):341–346 (1984).

De Tata, et al., "Beneficial Effects of the Oral Administration of Vanadyl Sulphate on Glucose Metabolism in Senescent Rats ", Journal of Gerontology 48(5):B191–B195 (1993).

Defronzo et al., "Insulin Resistance; A Multifaceted Syndrome Responsible for NIDDM, Obesity, Hypertension, Dyslipidemia, and Atherosclerotic Cardiovascular Disease" Diabetes Care 14 (3):173–194 (1991).

DeFronzo, R.A., "Efficacy Of Metformin in Patients with Non–Insulin–Dependent Diabetes Mellitus" The New England Journal of Medicine 33 (9):541–549 (1995).

Dehghani et al., "Effect of Vanadyl Sulphate on Glucose Homeostasis in Severe Diabetes Induced by Streptozotocin in Rats", Indian J. Med Res. 106: 481–585 (1997).

Diabetes Pro Health " Akesis Pharmaceuticals Inc". (Pamphlet) Product first used no earlier than Jun. of 1997.

Diaetes Pro Health Inc. " Pro Health Pak" ( labels) Product described in label first sold no earlier than Jun. of 1997.

Diabetes Pro Health Inc. " Pro Health Pak" ( labels) Product described in label first sold no earlier than Mar. of 1998.

Diabetes Pro Health Inc. " Pro Health Pak" ( labels) Product described in label first sold no earlier than Oct. of 1999.

Dieber–Rotheneder et al., "Effect of Oral Supplementation with D–α–tocopherol on the vitamin E content of human low density lipoproteins and resistance to oxidation", Journal of Lipid Research 32: 1325–1332 (1991).

Domingo et al., "Administration of Vanadyl Sulfate by Gavage does not Normalize Blood Glucose Lvels in Streptozotocin–induced Diabetic Rats", Research Communications in Chemical Pathology and Pharmacology 75 (3) : 369–372 (Mar. 1992).

Domingo et al., "Tiron administration minimizes the toxicity of vanadate but not its insulin mimetic properties in diabetic rats," Life Sciences (1992) 50/18 (1311–1317), XP000901833.

Donadio, et al., "Platelet–Inhibitor Treatment of Diabetic Nephropathy: A 10–Year Prospective Study" Mayo Clin. Proc. 63:3–15 (1988).

Dubyak and Kleinzeller, "The Insulin–mimetic Effects of Vanadate in Isolated Rat Adipocytes" The Journal of Biological Chemistry 255 (11):5306–5312 (1980).

ETDRS Investigators, "Aspirin Effects on Mortality and Morbid in Patients With Diabetes Mellitus" JAMA 268 (10):1292–1300 (1992).

Evans and Bowman, "Chromium Picolinate Increases Membrane Fluidity and Rate of Insulin Internalization", Journal of Inorganic Biochemistry 46: 243–250 (1992).

Evans and Pouchnik, " Composition and Biological Activity of Chromium—Pyridine Carboxylate Complexes", Journal of Inorganic Biochemistry 49 :177–187 (1993).

Evans W. G., "The Effect of Chromium Picolinate on Insulin Controlled Parameters in Humans," Int. J. Biosocial Med. Research 11 (2) 163–180 (1989).

Ewald, et al., "Hypomagnesemia in Diabetic Children" Acta Padiatr Scand 72:367–371 (1983).

Expert Panel on Detection, Evaluation, and Treatment of High Blood Cholesterol in Adults, "Summary of the Second Report of the National Cholesterol Education Program (NCEP) Expert Panel on Detection, Evaluation, and Treatment of High Blood Cholesterol in Adults (Adult Treatment Panel 11)" JAMA 269 (23):3015–3023 (1993).

Foot et al., "The Effects of Orthovanadate, Vanadyl and Peroxides of Vanadate on Glucose Metabolism in Skeletal Muscle Preparations in Vitro", Molecular and Cellular Biochemistry 109; 157–162 (1992).

Franz et al., "Nutrition Principles for the Management of Diabetes and Related Complications" Diabetes Care 17 (5):490–518 (1994).

Freund et al., "Chromium Deficiency During Total Parenteral Nutrition" JAMA 241 (5):496–498 (1979).

Grant et al., "Chromium and Exercice Training: effect on obese women", Medicine & Science in Sports & Exercice, pp. 992–998 (1997).

Gunnar et al., "Recommendations for Angioplasty after Intravenous Thrombolysis," JAAC, 16(2):249–292 (1990).

Haffner et al., "Cardiovascular Risk Factors in Confirmed Prediabetic Individuals; Does the Clock for Heart Disease Start Ticking Before the Onset of Clinical Diabetes?"JAMA 263 (21):2893–2898 (1990).

Haffner et al., "Insulin Resistance Implications for Type II Diabetes Mellitus and Coronary Heart Disease," The American Journal of Medicine, 103:152–162 Aug. (1997).

Haffner et al., "Prospective Analysis of the Insulin–Resistance Syndrome (Syndrome X)" Diabetes 41:715–722 (1992).

Halberstam et al, "Oral Vanadyl Sulfate Improves Insulin Sensitivity in NIDDM but Not in Obese Nondiabetic Subjects" Diabetes 45:659–666 (1996).

Hansson et al., Effects of Intensive Blood–Pressure Lowering and Low–Dose Aspirin in Patients with Hypertension: Principal Results of the Hypertension Optimal Treatment (HOT) Randomised Trial, The lancelet, 351:1755–1762 Jun. (1998).

Harris et al., "Onset of NIDDM Occurs at Least 4–7 Yr Before Clinical Diagnosis" Diabetes Care 15 (7):815–819 (1992).

Hatwal et al., "Association of hypomagnesemia with diabetic retinopathy" Acta Ophthalmologica 67:714–716 (1989).

Heath et al., "Platelet Adhesiveness and Aggregation in Relation to Diabetic Retinopathy" Diabetologia 7.308–315 (1971).

Hennekens et al., "An Overview of The British and American Aspirin Studies" The New England Journal of Medicine 318(14):923–924 (1988).

Hermann et al., "Therapeutic Comparison of Metformin and Sulfonylurea, Alone and in Various Combinations" Diabetes Care 17 (10):1100–1109 (1994).

Hirsh et al., "Aspirin and Other Platelet–Active Drugs; The Relationship Among Dose, Effectiveness, and Side Effects" Chest 108 (4):247S–257S (1995).

InterHealth Company., "Facts About Chromium Nutrition; Fact Sheet #1: The Importance of Niacin–Bound Chromium in Human Nutrition", (Jul. 21, 1992).

InterHealth Company., "Facts About Chromium Nutrition; Fact Sheet #2: Niacin–Bound Chromium Compounds Vary; ChromeMate's Oxygen—Coordinated Complex Found 18 Times More Potent", (Oct. 5, 1992).

InterHealth Company., "Facts About Chromium Nutrition; Fact Sheet #3 : UC Study finds ChromeMate More Biovalaible than Chromium Picolinate, Chromium Chloride" (Oct. 14, 1992).

Inzucchi et al., "Efficacy and Metabolic Effects of Metformin and Troglitazone in Type II Diabetes Mellitus," The New England Journal of Medicine, 338(13):867–872 (1998).

Jain, et al., "Some Metabolic Facets of Magnesium in Diabetes Mellitus" Jr. Asso. Phys. Ind 24:827–831 (1976).

Jarrett et al., "The Bedford Survey: Ten Year Mortality Rates in Newly Diagnosed Diabetics, Borderline Diabetics and Normoglycaemic Controls and Risk Indices for Coronary Heart Disease in Borderline Diabetics" Diabetologia 22:79–84 (1982).

Jeejeebhoy, "Chromium deficiency, glucose intolerance, and neuropathy reversed by chromium supplementation, in a patient receiving long–term total parenteral nutrition" The American Journal of Clinical Nutrition 30:531–538 (1977).

Joffres et al., "Relationship of magnesium intake and other dietary factors to blood .pressure: the Honolulu heart study" Am J Clin Nutr 45:469–475 (1987).

Jovanovic "Chromium Supplementation for Women with Gestational Diabetes Mellitus" The Journal of Trace Elements in Experimental Medicine 12:91–97 (1999).

Julkunen–Tütto and Talivanainen, "The Effect of the Sample Preparation Method of Extractable Phenolics of Salicaceae Species" Planta Medica 55:55–61 (1989).

Kannel, W. B., "Lipids, diabetes, and coronary heart disease: Insights from the Framingham Study" Am Heart J 110 (5):1100–1107 (1985).

Kaplan, N. M., "The Deadly Quartet; Upper–Body Obesity, Glucose Intolerance, Hypertriglyceridemia, and Hypertension" Arch Intern Med 149:1514–1520 (1989).

Klein et al., "Visual Impairment in Diabetes" *Ophthalmology* 91 (1):1–9 (1984).

Koskinen et al., "Coronary Heart Disease Incidence in NIDDM Patients In The Helsinki Heart Study" *Diabetes Care* 15 (7):820–825 (1992).

Krolewski et al., "Evolving Natural History of Coronary Artery Disease in Diabetes Mellitus" *The American Journal of Medicine* 90 (suppl. 2A):2A–56S–2A–61S (1991).

Krumholz et al., "Aspirin for Secondary Prevention after Acute Myocardial Infarction in the Elderly: Prescribed Use and Outcomes" *Ann Intern Med* 124:292–298 (1996).

Kushi, et al., "Dietary Antioxidant Vitamins and Death From Coronary Heart Disease in Postmenopausal Women" *The New England Journal of Medicine* 334 (18):1156–1162 (1996).

Kuusisto et al., "NIDDM and Its Metabolic Control Predict Coronary Heart Disease in Elderly Subjects" *Diabetes* 43:960–967 (1994).

Lee and Reasner, "Beneficial Effect of Chromium Supplementation on Serum Triglyceride Levels in NIDDM" *Diabetes Care* 17 (12):1449–1452 (1994).

Lee et al., "Dose Effects of Aspirin on Gastric Prostaglandins Stomach Mucosal Injury" *Annals of Internal Medicine* 120 (3):184–189 (1994).

Lefavi et al., " Lipid–Lowering Effect of a Dietary Nicotinic Acid—Chromium(III) Complex in Male Athletes", The FASEB JOURNAL, 5 (6) A1645 (1991) (Abstract).

Levin et al., "Tissue Magnesium Status in Diabetes Mellitus" *Diabetologia* 21:131–134 (1981).

Liu and Morris, "Relative chromium response as an indicator of chromium status" *The American Journal of Clinical Nutrition* 31:972–976 (1978).

Madan et al. " An Antiatherogenic role for folic acid in experimental Diabetes", J. Clin. Biochem. Nutr. 18(3):157–164 (1995).(Abstract).

Malabu, et al., "Effects of Chronic Vanadate Administration in the STZ–Induced Diabetic Rat; The Antihyperglycemic Action of Vanadate. Is Attributable Entirely to Its Suppression of Feeding" *Diabetes* 43:9–15 (1994).

Margolis et al., "Clinical Features of Unrecognized Myocardial Infarction–Silent and Symptomatic; Eighteen Year Follow–up: The Framingham Study" *The American Journal of Cardiology* 32 (1):1–7 (1973).

Marier, J. R., "Cardio–Protective—Contribution of Hard Waters to Magnesium In–Take" *Rev. Can. Biol.* 37 (2):115–125 (1978).

Mather et al., "Hypomagnesaemia in Diabetes" *Clinica Chimica Acta* 95:235–242 (1972) 27.:1075–1077 (1978).

McCarty, "Complementary measures for promoting insulin sensitivity in skeletal muscle," Medical Hypotheses, 51(6) 451–64 (1998) XP–00908774.

McNair et al., "Hypomagnesaemia, a Risk Factor in Diabetic Retinopathy," Diabetes 27:1075–1077 (1978).

McNair et al., "Renal hypomagnesaemia in human diabetes mellitus: its relation to glucose homeostasis" *European Journal of Clinical Investigation* 12:81–85 (1982).

McNeill et al., "Oral Vanadium and Lowering of Blood Glucose" *Diabetes* 43:1268 (1994).

McPhillips et al., "Cardiovascular Disease Risk Factors Prior to the Diagnosis of Impaired Glucose Tolerance and Non–Insulin Dependent Diabetes Mellitus in a Community of Older AdultS" *American Journal of Epidemiology* 131 (3):443–453 (1990).

Meinert et al., "Mortality Results; A Study of the Effects of Hypoglycemic–Agents on Vascular Complications in Patients with Adult–Onset Diabetes" *The University Group Diabetes Program Chptr* 11:786–830 (1961).

Mertz W., "Effects and Metabolism of Glucose Tolerance Factor" *Nutrition Reviews* 33 (5):1.29–135 (1975).

Meyerovitch et al., "Oral Administration of Vanadate Normalizes Blood Glucose Levels in Streptozotocin–Treated Rats," The Jornal of Biological Chemistry, 262(14):6658–6662 (1987).

Mongold et al., "Toxicological Aspects of Vanadyl Sulphate on Diabetic Rats: Effects on Vanadium Levels and Pancreatic B–Cell Morphology" *Pharmacology & Toxicology* 67:192–198 (1990).

Mooradian, A. D., "Selected Vitamins and Mineral in Diabetes" *Diabetes Care* 17 (5):464–479 (1994).

Moore and Friedl, "Physiology of Nutritional Supplements: Chromium Picolinate and Vanadyl Sulfate," National Strength and Conditioning Associaton Journal 14:(3) 47–48 (1992).

Morris et al, "Effect of Glucose Loading on Concentrations of Chromium in Plasma and Urine of Healthy Adults" *Clinical Chemistry* 34 (6):1114–1116 (1988).

Morris et al., "Plasma Chromium and Chromium Excretion in Diabetes" *Clinical Chemistry* 31 (2):334–335 (1985).

Morris et. al., "Correlations between Abnormalities In Chromium and Glucose Metabolism In a Group of Diabetics" *Clinical Chemistry* 34 (7):1525–1526 (1988).

Nadler et al., "Intracellular Free Magnesium Deficiency Plays a Key Role in Increased Platelet Reactivity in Type II Diabetes Mellitus" *Diabetes Care* 15 (7):835–841 (1992).

Newman et al., "Serum Chromium and Angiograhically Determined Coronary Artery Disease" *Clin. Chem.* 24 (4):541–544 (1978).

Offenbacher and Pi–Sunyer, "Beneficial Effect of Chromium–rich Yeast on Glucose Tolerance and Blood Lipids in Elderly Subjects" *Diabetes* 29:919–925 (1980).

Olin et al., " Comparative Retention/Absorption of Chromium (Cr) from Cr Chloride(CrCI), Cr Nicotinate (CrNic), and Cr Picolinate (CrPic) in a Rat Model," (Reprint of Abstract and Data Presented at $33^{rd}$ Annual Meeting of the American College of Nutrition, Oct. 10, 1992).

Opkere et al., "Failure of oral metavanadate to correct streptozotocin–induced diabetes in rats", Diabetic Medicine Supplement 2 to vol. 5: A30 (p.8) (1988) (Abstract).

Orchard and Strandness, "Assessment of Peripheral Vascular Disease in Diabetes" *Circulation* 88 (2):819–828 (1993).

Pagano, G. "Metformin Reduces Insulin Requirement in Type 1 (Insulin–Dependent) Diabetes" *Diabetologia* 24:351–354 (1983).

Paolisso et al., "Daily Vitamin E Supplements Improve Metabolic Control But Not Insulin Secretion in Elderly Type H Diabetic Patients" *Diabetes Care* 16 (11):1433–1437 (1993).

Paolisso et al., "Dietary magnesium supplements improve B–cell response to glucose and arginine in elderly non–insulin dependent diabetic subjects" *Acta Endocrinologica* 121: 16–20 (1989).

Paolisso et al., "Improved Insulin Response and Action by Chronic Magnesium Administration in Aged NIDDM Subjects" *Diabetes Care* 12 (4):265–69 (1989).

Paolisso et al., "Magnesium and glucose homeostatis" *Diabetologia* 33:511–514 (1990).

Paolisso et al., "Pharmacologic doses of vitamin E improve insulin action in healthy subjects and non–insulin–dependent diabetic patients" *Am J Clin Nutr* 57:650–656 (1993).

Pederson et al., "Long–Term Effects of Vanadyl Treatment on Streptozocin–Induced Diabetes in Rats," Diabetes, 38:1390–1395 (1989).

Perfetti et al., "Novel Therapeutic Strategies for the Treatment of Type 2 Diabetes," Diabetes/Metabolism Reviews, 14:207–225 (1998) XP–000908775.

Potter et al., "Glucose Metabolism in Glucose–Intolerant Older People During 'Chromium Supplementation" Metabolism 34 (3):199–204 (1985).

Press et al., "The Effect of Chromium Picolinate on Serum Cholesterol and Apolipoprotein Fractions in Human Subjects" West J Med 152:41–45 (1990).

Preuss et al., "Effects of Different Chromium Compounds on Blood Pressure and Lipid Peroxidation in Spontaneously Hypertensive Rats", Clinical Nephrology 47(5) 325–330 (1997).

Preuss, H., "Effects of Glucose/Insulin Perturbations on Aging and Chronic Disorders of Aging: The Evidence",The Journal of the American College of Nutrition, vol. 16, No. 5, 397–403 (1997).

Ravina et al., "Clinical Use of the Trace Element Chromium (III) in the Treatment of Diabetes Mellitus," The Journal of Trace Elements in Experimental Medicine 8:183–190 (1995).

Ravina et al., "Reversal of corticosteroid–induced diabetes mellitus with supplemental chromium," British Diabetic Associates, Diabetic Medicine, 16:164–167 (1999).

Reaven, G. M., "Role of Insulin Resistance in Human Disease" Diabetes 37:1595–1607 (1988).

Reinhart, R. A., "Magnesium Metabolism; A Review With Special Reference to the Relationship Between Intracellular Content and Serum Levels" Arch Intern Med 148:2415–2420 (1988) Role of Intracellular Free Magnesium The American Journal of Hypertension 3 (5)(Part 1):373–379 (1990).

Resnick et al., "Hypertension and Peripheral Insulin Resistance; Possible Mediating Role of Intracellular Free Magnesium" The American Journal of Hypertension 3 (5) (Part 1):373–379 (1990).

Resnick, L. M., "Cellular Calcium and Magnesium Metabolism in the Pathophysiology and Treatment of Hypertension and Related Metabolic Disorders" The American Journal of Medicine 93 (Suppl 2A):2A–I IS 2A–20S (1992).

Riales et al., "Effect of Chromium Chloride Supplementation on Glucose Tolerance and Serum Lipids Including High–Density Lipoprotein of adult Men," The American Journal of Clinical Nutrition, 34:2670–2678 (1981).

Rimm et al., "Vitamin E And Risk Of Coronary Heart Disease In Men" The New England Journal of Medicine 328 (20):1450–1456 (1993).

Roeback et al., "Effects of Chromium Supplementa–tion on Serum High–Density Lipoprotein Cholesterol Levels in Men Taking Beta–Blockers" Annals of Internal Medicine 115 (12):917–924 (1991).

Rubin et al., "Health Care Expenditures for People with Diabetes Mellitus, 1992" Journal of Clinical Endocrinology and Metabolism 78 (4):809A–809F (1994).

Rude, R.K., "Physiology of Megnesium Metabolism and the Important Role of Magnesium in Potassium Deficiency" The American Journal of Cardiology 63:31G–34G (1989).

Ryzen et al., "Low blood mononuclear cell magnesium in intensive cardiac care unit patients" American Heart Journal 111:475–480 (1986).

Saad et al., "Sequential Changes In Serum Insulin Concentration During Development Of Non–Insulin–Dependent Diabetes" The Lancet pp 1356–1359 (1989).

Saltiel and Olefsky, "Thiazolidinediones in the Treatment of Insulin Resistance and Type II Diabetes" Diabetes 45:1661–1669 (1996).

Schwartz et al., "Effect of Troglitazone in Insulin–Treated Patients with Type II Diabetes Mellitus," The New England Journal of Medicine, 338(13):861–866 (1998).

Seelig and Heggtveit, "Magnesium interrelationships in ischemic heart disease: a review" The American Journal of Clinical Nutrition 27:59–79 (1974).

Seelig, M., "Cardiovascular Consequences of Magnesium Deficiency and Loss: Pathogenesis, Prevalence and Manifestations–Magnesium and Chloride Loss in Refractory Potassium Repletion" The American Journal of Cardiology 63:4G–21G (1989).

Sjogren et al., "Magnesium, Potassium and Zinc Deficiency in Subjects with Type II Diabetes Mellitus" Acta Med Scand 224:461–465 (1988).

Sjogren et al., "Oral Administration of Magnesium Hydroxide to Subjects with Insulin Dependent Diabetes mellitus: Effects on Magnesium and Potassium Levels and on Insulin Requirements" Magnesium 7:117–122 (1988).

Spears, J.W., "Reevaluation of the metabolic essentiality of the minerals: Review," Asian–Australasian Journal of Animal Sciences, Sep. 1999 12:6, 1002–1008, XP000901962 Abstract.

Stamler et al., "Diabetes, Other Risk Factors, and 12–Yr Cardiovascular Mortality for Men Screened in the Multiple Risk Factor Intervention Trial" Diabetes Care 16 (2):434–444 (1993).

Stampfer et al., "Vitamin E Consumption And The Risk Of Coronary Disease In Women" The New England Journal of Medicine 328 (20):1444–1449 (1993).

Stearns et al., "Chromium (III) picolinate produces chromosome damage in Chinese hamster ovary cells[1]," The FASEB Journal 9:1643–1649 ( Dec. 1995).

Steinberg et al., "Antioxidants in the Prevention of Human Atherosclerosis" Circulation (6):2337–2345 (1992).

Steinberg et al., "Beyond Cholesterol; Modifications of Low–Density Lipoprotein That Increase Its Atherbgenicity " The New England Journal of Medicine 320 (14):915–924 (1989).

Stephens et al., "Randomised controlled trial of vitamin E in the patients with coronary disease: Cambridge Heart Antioxidant Study (CHAOS)" The Lancet 347:781–786 (1996).

Stewart and Basten, "Lupus Erythematosus and Brain Scanning," Annal of Internal Medicine, 83(5):733–738 (1975).

The RISC Group, "Medicine Science; Risk of myocardial infarction and death during treatment with low dose aspirin and intravenous heparin in men with unstable coronary artery disease" The Lancet 336:827–830 (1990).

The SALT Collaborative Group, "Swedish Aspirin Low––dose Trial (SALT) of 75 mg aspirin as secondary prophylaxis after cerebrovascular ischaemic events" The Lancet 338 (8779):1345–1349 (1991).

Thomas and Gropper,. "Effect of Chromium Nicotinic Acid Supplementation on Selected Cardiovascular Disease Risk Factors", Biological Trace Element Research 55(3): 297–305 (1996).

Thompson, et al., "Studies of Vanadyl Sulfate as a Glucose Lowering Agent in STZ–Diabetic Rats" Biophemical and Biopysical Research Communications 197 (3):1549–1555 (1993).

Tomlinson, "Future Prevention and Treatment of Diabetic Neuropathy," Diabetes & Metabolism (Paris)24 (Suppl. 3):79–83 (1998).

Tosiello L., "Hypomagnesemia and Diabetes Mellitus" Arch Intern Med 156:1143–1148 (1996).

Trip et al, "Platelet Hyperreactivity and Prognosis in Survivors of Myocardial Infarction" The New England Journal of Medicine 322 (22):1549–1554 (1990).

Tuman and Doisy, "Metabolic Effects of the Glucose Tolerance Factor (GTF) in Normal and Genetically Diabetic Mice" *Diabetes* 26 (9):820–826 (1977).

United Kingdom Prospective Diabetes Study Group, "United Kingdom prospective diabetes study (UKPDS) 13: relative efficacy of randomly allocated diet, sulphonylurea, insulin, or metformin patients with newly diagnosed non–insulin dependent diabetes followed for three years" *BMJ* 310:83–88 (1995).

Urberg and Zemel., " Evidence for Synergism Between Chromium and Nicotinic Acid in the Control of Glucose Tolerance in Elderly Humans", Metabolism 36(9): 896–899 (Sep. 1987).

Urberg et al., " Hypocholesterolemic Effects of Nicotinic Acid and Chromium Supplementation", The Journal of Family Practice 27:(6) 603–606 (1988).

Verlangieri and Bush, "Effects of d–α–Tocopherol Supplementation on Experimentally Induced Primate Atherosclerosis" *Journal of the American College of Nutrition* 11 (2):131–138 (1992).

Walter et al., "The Effect of Oral Chromium Picolinate on Glycemic Responses and Lipid Profiles in Patients with Type II Diabetes Mellitus", Diabetes 42 ( Suppl.):146( May 1993).

Whang, R., "Magnesium Deficiency: Pathogenesis, Prevalence, and Clinical Implications" *The American Journal of Medicine* 82 (suppl 3A):24–29 (1987).

Widman, "The Dose–Dependent Reduction in Blood Pressure Through Administration of Magnesium; A Double Blind Placebo Controlled Cross–Over Study" *The American Journal of Hypertension, Inc.* 6:41–45 (1993).

Wilson and Gondy., "Effects of Chromium Supplementation on Fasting Insulin Levels and Lipid Parameters in Healthy, Non–obese Young Subjects", Diabetes Research and Clinical Practice 28: 179–184 (1995).

Woods and Fletcher, "Long–term outcome after intravenous magnesium sulphate in suspected acute myocardial infarction: the second Lelcester Intravenous Magnesium Intervention Trial (LIMIT–2)" *The Lancet* 343:816–819 (1994).

Woolliscroft and Barbosa, "Analysis of Chromium Induced Carbohydrate Intolerance in the Rat" *J. Nutr.* 107:1702–1706 (1977).

Ziegler et al., "Treatment of Symptomatic Diabetic Peripheral Neuropathy with the anti–oxidant–lipoic acid", Diabetologia 38:1425–1433 (1995).

Abraham et al., "The Effects of Chromium Supplementation on Serum Glucose and Lipids in Patients with and without Non–Insulin–Dependent Diabetes," Metabolism, 41(7):768–771 (1992).

Blondel et al., "In Vivo Insulin Resistance in Streptozotocin–Diabetic Rates—Evidence for Reversal Following Oral Vanadate Treatment," Diabetologia 32:185–190 (1989).

Colwell, John A., "DCCT Findings: Applicability and Implications for NIDDM," Diabetes Reviews, 2(3):277–291 (1994).

Cunningham, John J., "Micronutrients as Nutriceutical Interventions in Diabetes Mellitus," Journal of the American College of Nutrition, 17(1):7–10 (1998).

Dornan et al., "Double–Blind Evaluation of Efficacy and Tolerability of Metformin in NIDDM," Diabetes Care, 14(4):342–344 (1991).

Jovanovic–Peterson et al., "Chromium Supplementation for Gestational Diabetic Women (GDM) Improves Glucose Tolerance and Decreases Hyperinsulinemia," Diabetes, Abstract, 45(2) (1996).

Lardinois, Claude, "Type 2 Diabetes: Glycemic Targets and Oral Therapies for Older Patients," Geriatrics, 53(11):22–39 (1998).

"Chromium picolinate for good health?," Biolifeplus.com, 'Online! Oct. 16, 1999, XP002135607, www.biolifeplus.com/library/chromium.html, retrieved on Apr. 5, 2000.

Bahadori et al., "Effects of Chromium Picolinate on Insulin Levels and Glucose Control in Obese Patients with Type–II Diabetes Mellitus," *Diabetes*, Abstract Book, 59th Scientific Sessions, pp. A349 (1999).

ChromeMate: Research Summary (1993).

Salonen et al., "Increased risk of non–insulin dependent diabetes mellitus at low plasma vitamin E concentrations: a four year follow up study in men" *BMJ* 311, pp. 1124–1127 (1995).

Diabetes Pro Health Inc., "Introducing A Nutritional Supplement Specifically Formulated For Adults With Diabetes & Pre–Diabetes" (1997).

Verma et al., "Metformin improves cardiac function in isolated streptozotocin–diabetic rat hearts," *American Journal of Physiology*, (1994).

Haupt et al., "Metformin and its role in the management of type–2–diabetes," *Medizinische Klinik*, Munich, (1997).

Anderson et al., "Elevated intakes of supplemental chromium improve glucose and insulin variables in individuals with type 2 diabetes," *Diabetes*, vol. 46, No. 11, pp. 1786–1791 (1997).

Ziegler et al., "Treatment of symptomatic diabetic peripheral neuropathy with the anti–oxidant α–lipoic acid: A 3–week multicenter randomized controlled trial (Aladin Study)," Diabetes–Forschungsinstitut, (1995).

Pote et al., "An antiatherogenic role for folic acid in experimental diabetes," *Journal of Clinical Biochemistry and Nutrition*, vol. 18(3), pp. 157–164 (1995).

Mark et al., "Hypoglycemic effects of the novel antidiabetic agent repaglinide in rats and dogs," *British Journal of Pharmacology*, vol. 121(8), pp. 15497–1604 (1997).

* cited by examiner

COMPOSITIONS AND METHODS FOR TREATMENT FOR GLUCOSE METABOLISM DISORDERS

RELATED APPLICATION INFORMATION

This Application is a Continuation-in-Part of application Ser. No. 09/156,102, filed Sep. 17, 1998, now U.S. Pat. No. 6,376,549, and this Application claims the benefit of priority under 35 U.S.C. section 119(e) to Provisional Application 60/126,489, filed Mar. 26, 1999, both of which Applications are hereby incorporated by reference in their entirety.

BACKGROUND OF THE INVENTION

Diabetes adversely affects the way the body uses sugars and starches which, during digestion, are converted into glucose. Diabetes mellitus is generally caused in almost all instances by diminished rates of insulin secretion (absolute or relative) by the beta cells of the islets of Langerhans in the pancreas or by reduced insulin sensitivity. Insulin, a hormone produced by the pancreas, makes the glucose available to the body's cells for energy. In muscle, adipose (fat), and connective tissues, insulin facilitates the entry of glucose into the cells by an action on the cell membranes. The ingested glucose is normally converted in the liver to $CO_2$ and $H_2O$ (50%); to glycogen (5%); and to fat (30–40%), the latter being stored in fat depots. Fatty acids from the adipose tissues are circulated, returned to the liver for re-synthesis of triacylglycerol and metabolized to ketone bodies for utilization by the tissues. The fatty acids are also metabolized by other organs.

The net effect of insulin is to promote the storage and use of carbohydrates, protein and fat. Insulin deficiency is a common and serious pathologic condition. Diabetes is commonly divided into two types: Type 1 diabetes (juvenile-onset, insulin-dependent diabetes mellitus [IDDM]) that usually, but not always, begins in early life, and Type 2 diabetes (maturity-onset diabetes, non-insulin dependent diabetes mellitus [NIDDM]) that usually, but not always, begins in later life. In Type 1 diabetes, the pancreas produces little or no insulin, and insulin must be injected daily. In Type 2 diabetes, the pancreas retains the ability to produce insulin and in fact may produce higher than normal amounts of insulin, but the amount of insulin is relatively insufficient, or less than fully effective, because of cellular resistance to insulin. Type 2 diabetes may present as non-obese NIDDM, obese NIDDM, or maturity-onset diabetes of the young (MODY). Type 1 is likely to occur in those with a family history of diabetes and is characterized by blurred vision, itching, unusual thirst, drowsiness, obesity, fatigue, skin infections, slow healing, and tingling or numbness in the feet.

Type 1 Diabetes

Type 1 diabetes accounts for around ten percent of all cases of diabetes mellitus. The action of Type 1 diabetes is to cause hyperglycemia (elevated blood glucose concentration) and a tendency towards diabetic ketoacidosis (DKA). Currently treatment requires chronic administration of insulin. No single standard exists for patterns of administration of insulin and treatment plans vary and may be selected from one of three treatment regimens: conventional, multiple subcutaneous injections, or continuous subcutaneous insulin infusion. Conventional insulin therapy involves the administration of one or two injections a day of intermediate-activity insulin such as zinc insulin or isophane insulin with or without the addition of small amounts of regular insulin. Regular insulin has a duration of action lasting from 3 to 8 hours, whereas other forms of insulin are absorbed slowly from the injection site and therefore have effects that may last as long as ten to forty-eight hours. The multiple subcutaneous insulin injection technique involves administration of intermediate- or long-acting insulin in the evening as a single dose together with regular insulin prior to each meal. Continuous subcutaneous insulin infusion involves the use of a small battery-driven pump that delivers insulin subcutaneously into the abdominal wall, usually through a butterfly needle. Insulin is delivered at a basal rate continuously throughout the day, with increased rates programmed prior to meals. Insulin may also be delivered by way of an implant that is administered parenterally, or by way of slow-release formulations.

Type 2 Diabetes

Type 2 diabetes is marked by hyperglycemia that is not linked with DKA. Sporadic or persistent incidence of hyperglycemia may be controlled by administering insulin. Uncontrolled hyperglycemia may transiently adversely affect the insulin-producing cells of the pancreas (the beta-islet cells), which may eventually result in greater insulin deficiencies. In most Type 2 diabetic subjects, the fundamental defects to which such abnormalities may be traced include (1) a reduced entry of glucose into various "peripheral" tissues, and (2) an increased liberation of glucose into the circulation from the liver. There is therefore an extracellular glucose excess and an intracellular glucose deficiency. There is also a decrease in the entry of amino acids into muscle and an increase in lipolysis. The cumulative effect of these diabetes-associated abnormalities may be severe blood vessel and nerve damage. Type 2 diabetic subjects may be treated with insulin, if necessary.

Type 2 often develops in subjects of certain at risk populations. Obesity predisposes an individual to Type 2 diabetes due to long-term effects on insulin resistance. If the beta-cells are compromised, diabetes may well ensue. Type 2 also develops from to the at risk population of individuals with gestational diabetes mellitus (GDM). Pregnancy normally is associated with progressive resistance to insulin-mediated glucose disposal. In fact, insulin sensitivity is lower during late pregnancy than in nearly all other physiological conditions. The insulin resistance is thought to be mediated in large part by the effects of circulating hormones such as placental lactogen, progesterone, and cortisol, all of which are elevated during pregnancy. In the face of the insulin resistance, pancreatic beta-cell responsiveness to glucose normally increases nearly 3-fold by late pregnancy, a response that serves to minimize the effect of insulin resistance on circulating glucose levels. Thus, pregnancy provides a major "stress-test" of the capacity for beta-cells to compensate for insulin resistance.

Other populations thought to be at risk for developing Type 2 diabetes are the elderly; certain minorities; persons with Syndrome X; persons with concomitant hyperinsulinemia; persons with insulin resistance characterized by hyperinsulinemia and by failure to respond to exogenous insulin; and persons with abnormal insulin and/or evidence of glucose disorders associated with excess circulating glucocorticoids, growth hormone, catecholamines, glucagon, parathyroid hormone, and other insulin-resistant conditions.

Treatment of Diabetes and its Complications

Diabetes has become a leading health care issue in the United States and other countries, accounting for one seventh of the national health care budget. The incidence of diagnosed diabetes has increased five-fold in America over the past 35 years, with currently 8 million diagnosed diabetic patients, another estimated 8 to 12 million undiagnosed diabetic individuals, and still an additional 23 million Americans with pre-diabetes, or impaired glucose tolerance (IGT). As the American populace continues its trend towards aging, obesity, and greater minority representation, the number of individuals who are diabetic and suffer from other glucose metabolism disorders is likely to increase.

Diabetic Complications and Symptoms

Although progress has been made in reducing the short term complications of diabetes, e.g. ketoacidosis, dehydration, and non-ketotic hyperosmolar coma, less progress has been made in preventing or minimizing the chronic complications of the disease, e.g. premature atherosclerosis, retinopathy, nephropathy, and neuropathy. It is estimated that a diabetic patient's life is shortened by 10 to 15 years, and those years of life are distinguished by significantly increased medical care costs as compared to a non-diabetic patient. Some complications of diabetes includes blindness and end-stage renal disease.

Another complication of diabetes mellitus is diabetic neuropathy (also called neuritis), which has been an unusually refractive complication of diabetes. Endoneural hypoxia is the overt cause of diabetic neuropathy. Early symptoms include numbness, irritation, and pain, usually in the extremities, and more advanced ones include gastroparesis and impotence. The conversion of the essential fatty acid (EFA) linolenic acid to gamma-linolenic acid (GLA) appears to be impaired in diabetics because of a lack of the enzymes delta-6-desaturase and/or delta 5-desaturase. Consequently, there is shortage of GLA and its metabolites, prostacyclin and prostaglandins, the chronic deficiencies of which contribute to the pathogenesis of diabetic neuropathy. Prostacyclin (PGI2) is a vasoprotective molecule with multiple physiological functions, and the enzyme cyclooxygenase (cox) is involved in its synthesis. Two isoforms of cox have been identified to date: cox-1, which produces both prostacyclin and anti-inflammatory prostaglandins, and cox-2, which produces both thromboxane $A_2$ ($TxA_2$) and some of the prostaglandins responsible for inflammation. Many therapeutics for pain management inhibit both cox-1 and cox-2, thereby reducing inflammation caused by prostaglandins produced by cox-2, but also inhibiting production of prostacyclin, which may exacerbate a prostacyclin deficiency resulting in neuropathy. In addition, neurotrophic factors, such as the superfamiliy of neurotrophins including nerve growth factor, may present an alternative pathogenic mechanism that results in neuropathy.

Another complication of diabetes is increased cardiovascular risk factor, especially among women. A man's risk of dying by heart disease doubles upon developing diabetes, whereas a woman's risk increases three to five-fold.

In particular, Type 2 diabetes presents a number of co-existent cardiovascular metabolic risk factors, e.g., insulin resistance, hyperinsulinemia, central obesity, hypertriglyceridemia, low HDL level, quantitatively abnormal LDL (diabetic dyslipidemia), hypertension, glucose intolerance, and elevated blood pressure. This state has been identified as "Syndrome X." These cardiovascular risk factors may precede the onset of diabetes by as much as a decade, and they may explain the presence of overt clinical cardiovascular disease in as many as 60% of newly diagnosed diabetic patients. For example, elevated glycated hemoglobin (HbA1c) is believed to be a risk marker for short-term mortality following acute myocardial infarction in non-diabetic subjects.

Diabetic dyslipidemia is another complication of diabetes and is of import to cardiovascular health. Plasma cholesterol and triglycerides are transported in lipoproteins (HDL, VLDL, and LDL). Dyslipoproteinemias are conditions in which the concentration and composition of these cholesterol- or triglyceride-carrying lipoproteins are abnormal. Elevated concentration of lipoproteins LDL and VLDL may accelerate the development of atherosclerosis, with the secondary possibilities of thrombosis and infarction. Evidence suggests that reduction of the concentration of lipoproteins LDL and VLDL in plasma may diminish the increased risk of atherosclerosis that accompanies hyperlipoproteinemia. Dyslipoproteinemias have been designated as either primary or secondary. Secondary dyslipoproteinemias involve complications of a more generalized metabolic disturbance, such as diabetes mellitus or excessive intake of ethanol. In contrast, primary dyslipoproteinemias are typically caused either by an inherited single-gene defect (monogenic dyslipoproteinemias) or a combination of multiple subtle genetic factors that act together with environmental ones (multifactorial or polygenic dyslipoproteinemias).

Evidence suggests that treatment of hyperlipoproteinemia may diminish or prevent atherosclerotic complications. For example, populations studies have shown that an elevated concentration of total cholesterol or LDL-cholesterol in plasma constitutes a major risk factor for the occurrence of atherosclerotic events. In the case of monogenic disorders, family studies have documented a markedly increased risk of vascular disease among affected members. These is evidence that reduction in plasma concentrations of LDL-cholesterol may reduce the risk of coronary heart disease (CHD).

Furthermore, there may be an excessive risk of cardiac mortality in diabetic patients even after adjusting for the co-existence of other cardiovascular risk factors such as hypertension, dyslipidemia, and cigarette smoking. This increase risk of cardiac mortality is secondary to both the atherogenicity of insulin resistance, which may precede the onset of diabetes by at least 8 years, and the atherogenicity of undiagnosed and uncontrolled hyperglycemia, which may be present for 9–12 years before diabetes is first diagnosed.

One means of attenuating the cardiovascular effects of diabetes, would involve earlier diagnosis and improved management of diabetes to reduce insulin resistance and control blood glucose. To this end, screening for risk factors for vascular complications followed by appropriate treatment may be appropriate.

Pharmacologic Interventions

Current drugs or anti-diabetic agents used for managing Type 2 diabetes that are well-known in the art generally fall within a number of categories: the biguanides, thiazolidinediones, the sulfonylureas, benzoic acid derivatives and glucosidase inhibitors. This drugs usually have distinct modes of action. The biguanides, e.g., metformin, are believed to prevent excessive hepatic gluconeogenesis. The thiazolidinediones are believed to act by increasing the rate of peripheral glucose disposal. The sulfonylureas, e.g., tolbutamide and glyburide, and the benzoic acid derivatives, e.g. repaglinide, lower plasma glucose by stimulating insulin secretion. The alpha-glucosidase inhibitors competitively inhibit alpha-glucosidase, which metabolizes carbohydrates, thereby delaying carbohydrate absorption and attenuating post-prandial hyperglycemia. In addition, there are a number of proposed therapies for treatment of diabetes that have not yet been approved for human use.

Because of the many complications that accompany diabetes and other glucose metabolism disorders, there remains a need to improve on treatment methods presently available, and to devise new means of treatments for preventing the onset and reducing the severity of Type 1 and 2 diabetes. In part, the present invention is directed to compositions comprised of a component and an anti-diabetic agent, and methods for using them, and programs thereof, that have been observed to alleviate or prevent diabetes and its associated sequelae. The subject compositions, and the methods of the using the same, may be used early in the course of developing diabetes and glucose metabolism disorders to reduce such complications.

SUMMARY OF THE INVENTION

The present invention represents new and important treatments or nutritional regimes for maintaining or promoting health, particularly the treatment of diabetes, pre-diabetes, and the reduction or avoidance of the onset of diabetes.

In certain embodiments, the present invention provides compositions, and methods of using the same, for regulating, modulating or altering glucose metabolism in a manner beneficial to the patient. Generally, various embodiments of the invention may be applied or tailored to specifically treat or address each condition described herein and others like them, including any condition or disorder related to glucose metabolism disorders. In certain embodiments, compositions of the present invention, and methods of using the same, are provided for preventing, reducing or treating in animal subjects (including humans and other mammals) one or more of the following physiological conditions: insulin resistance (the sensitivity of the cellular response to insulin), beta cell attrition, hyperinsulinemia, hyperglycemia, hepatic gluconeogenesis, onset of diabetes or diabetic symptoms, elevated HbA1c levels, and elevated or inappropriately controlled blood glucose levels. In certain embodiments, the present invention abates, or otherwise reduces the severity of, diabetes and other glucose metabolism disorders, including Type 1, Type 2, MODY, and IGT, and any related sequelae, including, for example, obesity, obesity-related hypertension, retinopathy, nephropathy, neuropathy, cataracts, coronary artery disease and arteriosclerosis. In certain embodiments, subject compositions contain one or more anti-diabetic agents and one or more other components. Such anti-diabetic agents and other such components may or may not be administered together or by the same means.

In other embodiments, the present invention provides supplements or compositions, and methods of using the same, for regulating, modulating or altering lipid metabolism in a manner beneficial to the patient. For example, the subject compositions, and methods of using the same, can be used to modulate at least one of body fat stores, blood pressure, hyperlipoproteinemia, hypertriglyceridemia, serum cholesterol level, HDL level and LDL level. In certain embodiments, the present invention abates or otherwise reduces the severity of dyslipidemia, atherosclerosis and CHD. In still other embodiments, the present invention provides compositions and supplements, and methods for using the same, to reduce appetite for cosmetic purposes or treatment of illness, dysfunction or obesity.

In certain embodiments, the present invention provides supplements or compositions containing an anti-diabetic agent and at least another component, and methods of using the same, for the long-term reduction and abatement of at least one of the foregoing disorders or conditions based on a therapeutic regimen. In certain aspects, the present invention contemplates monitoring such disorders or conditions as part of any therapeutic regimen, which may be administered over the short-term and/or long-term.

In certain embodiments, the invention compositions include at least a therapeutically effective amount of chromium and an anti-diabetic agent. In other embodiments, the invention compositions include at least a therapeutically effective amount of vanadium and an anti-diabetic agent. In still other embodiments, the present invention includes both chromium and vanadium and an anti-diabetic agent. In yet other embodiments, the chromium or vanadium of any composition is a bioavailable source. In addition, embodiments of the present invention may include any of the other components set forth herein and others known to those of skill in the art, including any agents, components or ingredients that are beneficial in the treatment or prevention of glucose metabolism disorders or any sequelae related to such disorders.

In some instances, the present invention is designed to regulate any of the physiological processes described herein so as to achieve a desired level of a physiological parameter (e.g., a HbA1c level of about 5). In certain embodiments, such a result is achieved without subjecting a patient to elevated levels of such a parameter. Such embodiments of the invention may prove useful in preserving health or reducing, preventing or delaying the on set of diabetes or diabetic symptoms without the patient experiencing the full thrust of such medical conditions. These aspects of the invention are particularly helpful in preventive care regimes.

In another aspect of the present invention, the subject compositions or supplements may be used in the manufacture of a medicament to treat any of the foregoing conditions or diseases. In certain embodiments, the present invention is directed to a method for formulating compositions or supplements of the present invention in a pharmaceutically acceptable excipient. In still other embodiments, the present invention contemplates compositions or supplements of the present invention for the treatment any of the foregoing conditions or diseases. It is preferred that each of the supplements and anti-diabeties are formulated as a tablet, capsule or other appropriate ingestible formulation, to provide a therapeutic dose in 10 tablets or fewer. It is more particularly preferred that a therapeutic dose is provided in five tablets or fewer, and it is most particularly preferred that a therapeutic dose is provided in three tablets or fewer.

In yet another aspect of the present invention, the use of a medicament for the treatment of a glucose metabolism disorder is provided whereby a sufficient amount of an inventive medicament is provided for treatment of a particular condition and instructions are provided to the patient for the desired medical treatment regimen. In particularly preferred embodiments, both an anti-diabetic agent and a supplement are provided, and the patient is instructed to ingest these concurrently.

In part, the present invention is directed to a dietary supplement that may be formulated for people individuals in an increased risk category as identified by any number of risk factors, including familial history. In certain embodiments, an object of the present invention is to screen subjects for a genetic predisposition to glucose metabolism disorders, such as IGT, Type 2 diabetes, or MODY, in order to begin administration of the supplements or compositions of the present invention, or methods of using the same, or programs thereof, to prevent or alleviate such disorders.

In another embodiment of the invention it will be desirable to include monitoring or diagnostic regimes or kits with composition or methods based on mineral and vitamins products described herein, and instructions for use of these compositions or methods.

In other embodiments, the present invention contemplates programs for prevention or treatment of any of the foregoing disorders or conditions. In some embodiments of such programs, one or more physiological parameters will be measured, and dosing and/or composition of supplement will be varied to reflect the health of the individual. Certain programs require that the patient ingest the supplement for a minimum time period, whereupon the same physiological parameters will be measured again to determine what affect the supplement may have caused. In certain embodiments, the programs call for changes in dosing, components, or formulation of the supplement depending on the results reported after an initial trial period on a program. In certain embodiments, programs of the present invention may require monitoring by the patients or additional treatment or prevention activities, such as dietary recommendations or exercise suggestions. In addition, in certain instances, the programs may include instructions for the patients concerning the scope and purpose of the program.

DETAILED DESCRIPTION OF THE INVENTION

1. Definitions

For convenience, before further description of the present invention, certain terms employed in the specification, examples, and appended claims are collected here. These definitions should be read in light of the rest of the disclosure and understood as by a person of skill in the art.

The term "anti-diabetic agent" shall mean any drug that is useful in treating, preventing, or otherwise reducing the severity of any glucose metabolism disorder, or any complications thereof, including any of the conditions, disease, or complications described herein. Anti-diabetic agents include insulin, thiazolidinediones, sulfonylureas, benzoic acid derivatives, alpha-glucosidase inhibitors, or the like. Other general categories of anti-diabetic agents which may be part of a subject composition include (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. §355(a) ("regulatory approved drug"); any agent that is or was subject to a human drug application under 21 U.S.C. §379(g) ("human drug"). (All references to statutory code for this definition refer to such code as of the original filing date of this Application.) Other anti-diabetic agents are disclosed herein, and are known to those of skill in the art. It is preferred that the inventive anti-diabetic compositions, as used herein, are capable of reducing HbA1c levels by at least a 10% change from the baseline, and it is more particularly preferred that the inventive anti-diabetic compositions, as used herein, are capable of reducing HbA1c levels by at least a 50% change from the baseline.

The term "bioavailable" means that a compound, composition, supplement, component, or material is in a form that allows for it, or a portion of the amount administered, to be absorbed by, incorporated to, or otherwise physiologically available to a subject to whom it is administered. In certain embodiments of the present invention, bioavailable sources of components of supplements or compositions of the present invention containing a transition metal, including chromium, vanadium, are contemplated, as discussed in more detail herein.

An embodiment of the invention is said to have an "insulinotropic activity" if it is able (i) to stimulate, or cause the stimulation of, the synthesis or expression of the hormone insulin, or (ii) to increase the half-life or the apparent potency of insulin in vivo. Insulin may be any naturally occurring form of the polypeptide, or any form of insulin, including any polypeptide that achieves the same effect of insulin, administered to a patient.

The phrases "parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal and intrasternal injection and infusion.

The term "modulation" as used herein refers to both upregulation (i.e., activation or stimulation) and downregulation (i.e. inhibition or suppression) of a response, or the two in combination or apart.

The phrase "pharmaceutically acceptable" refers to those supplements, components, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of components of compositions of the present invention.

The phrases "systemic administration," "administered systemically," "peripheral administration" and "administered peripherally" mean the administration of a subject supplement, composition, therapeutic or other material other than directly into the central nervous system, such that it enters the patient's system and, thus, is subject to metabolism and other like processes, for example, subcutaneous administration.

The phrase "therapeutically-effective amount" means that amount of supplement or composition which is effective for producing some desired therapeutic effect by, for example, modulating glucose metabolism at a reasonable benefit/risk ratio applicable to any medical treatment.

2. General Introduction

The present invention provides methods and compositions for modification and regulation of glucose and lipid metabolism, generally to reduce insulin resistance, hyperglycemia, hyperinsulinemia, obesity, dyslipidemia, hyperlipoproteinemia (such as VLDL), and to regulate body fat and more generally lipid stores, and, more generally, to improve of metabolism disorders, especially those associated with diabetes, obesity, atherosclerosis, or CHD.

For instance, in certain embodiments of the preset invention, administration of a subject supplement or composition, or methods of using the same, in an effective amount improves one or more aberrant indices associated with glucose metabolism disorders (e.g., glucose intolerance, insulin resistance, hyperglycemia, hyperinsulinemia, diabetic dyslipidemia, and Type 2 diabetes). In other embodiments, administration of a subject supplement, or methods thereof, in an effective amount improves aberrant indices associated with CHD or obesity.

In other embodiments, the supplements and compositions have anti-diabetic activities, and may be used in the treatment of disorders marked by aberrant glucose metabolism (including storage). In certain embodiments, supplements or compositions, or components thereof, of the present invention are useful as insulin enhancing or insulinotropic agents. The subject compositions or methods may be useful for the treatment and/or prophylaxis of a variety of disorders, including one or more of dyslipidemia, hyperglycemia, obesity, glucose tolerance insufficiency or impairment, insulin resistance, and diabetic complications.

In certain embodiments, the invention compositions include one or more anti-diabetic agents and one or more components described herein. In certain embodiments, such component constitutes a therapeutically effective amount of a bioavailable source of chromium. In other embodiments, such component constitutes a therapeutically effective amount of a bioavailable source of vanadium. In still other embodiments, the present inventin is directed towards a supplement or composition containing one or more additional components from the following group: magnesium, vitamin E, aspirin; alpha-lipoic acid; and folic acid.

In one embodiment, a supplement includes an effective amount of chromium polynicotinate and/or chromium picolinate as the chromium source, an effective amount of vanadyl sulfate as the vanadium source, an effective amount of magnesium as a either a complex of chloride or Krebs (citrate, fumarate, malate, glutarate or succinate), an effective amount of free 2R,4'R,8'R-alpha-tocopherol as the vitamin E source, or another effective source of vitamin E, an effective amount of standardized willow bark, an effective amount of folic acid and alpha-lipoic acid, as well as sufficient amounts of other vitamin and mineral sources.

In another aspect, the present invention is directed to supplements or compositions capable of preventing, treating, or otherwise reducing the severity of disorders of glucose metabolism. Insulin resistance is the pathophysiologic indicator of patients with IGT and Type 2 diabetes, which often occurs many years before clinically evident disease is present. As peripheral glucose use decreases, subjects may remain euglycemic, but hyperinsulinemic, as long as beta cells maintain sufficient insulin concentrations. Eventually, insulin resistance and rising plasma glucose levels outpace insulin production. The disease or condition progresses from insulin resistance with hyperinsulinemia to impaired glucose tolerance, resulting in modest increases in post-prandial glucose concentrations, followed by clinical diabetes and hyperglycemia. The supplements and compositions of the present invention, and methods of using the same, are intended to delay the onset of Type 2 diabetes and its associated sequelae by addressing disorders of glucose metabolism at an early stage.

The present invention also provides methods for enhancing the natural control of blood glucose levels in a person by daily administration of the subject composition and nutritional supplement. The present invention contemplates administration of a supplement of the present invention to control the blood sugar by reducing insulin resistance in diabetic and IGT patients, thereby preventing the chronic complications from developing in these high risk patients. There is also a need to provide an effective supplement for the treatment of diabetes and its symptoms prior to the onset of full-blown diabetes.

With respect to GDM, studies of insulin action and beta-cell function during pregnancy indicate that, during the third trimester, women with mild-moderate GDM have the same degree of insulin resistance as do non-diabetic pregnant women. However, studies during the second trimester and after pregnancy indicate that women with GDM are somewhat insulin resistant compared to women who maintain normal glucose tolerance during pregnancy. The main feature that distinguishes women with GDM from normal pregnant women during the third trimester, when all women are insulin resistant, is pancreatic beta-cell function. Most women develop GDM because their pancreatic beta-cells are unable to maintain enhanced insulin secretion in the face of insulin resistance. That inability is very similar to the beta-cell defect which has been observed in longitudinal studies of patients who develop Type 2 diabetes, a fact which may explain why women with GDM are at such high risk for Type 2 diabetes. GDM identifies women whose beta-cells will decompensate when faced with severe or chronic insulin resistance.

In another aspect, the present invention also provides for kits containing at least one dose of a subject supplement or composition, and often many doses, and other materials for a treatment regimen. For example, in one embodiment, a kit of the present invention contains sufficient subject composition for thirty days and equipment and supplies necessary to measure one or more indices relevant to glucose metabolism, such as blood glucose levels. In another embodiment, kits of the present invention contain all the materials and supplies, including supplements and compositions, for carrying out any methods of the present invention. In still another embodiment, kits of the present invention, as described above, additionally include instructions for the use and administration of the supplements and compositions.

In another aspect, the present invention provides for programs whereby the supplements or compositions of the present invention are ingested by a subject having a condition described herein, including subjects that are pre-diabetic. The program format of the present invention allows for a variety of variables to be addressed in providing composition and supplements of the present invention. Some of these variables include: one or more conditions to be addressed by any one program, compositions and supplements to be used in any such program, and dosing regimen of any such program. In certain instances, a program may include a kit of the present invention.

Many of the features of any program, including for example the dosing regimen, may be provided for in instructions to the subject participating in any program. Such instructions may, in certain embodiments, require the subject to decide whether to continue any program depending on the results obtained while on the program. The length of such trial period may vary with the particular program. Typically, trial periods may be between about one to about six or more months, and alternatively, the trial periods may be between one and three months.

In certain embodiments of such programs, the subject may be required to assess their progress on the program by monitoring a parameter relevant to their particular condition. In certain embodiments, a program directed to prevention or treatment of a glucose metabolism disorders may require subjects to monitor their HbA1c levels. After a certain period on such a program, during which the subject would have used the composition or supplement prescribed by the program in the manner dictated thereby, the program may require the subject to determine their HbA1c level. Depending on whether the HbA1c level changed by a particular amount, the subject may continue with the particular program, discontinue the program altogether, or alter the program. The foregoing decision may depend on the initial condition of the subject.

For example, in one embodiment of a program of the present invention, the dose of chromium administered to a patient in a composition varies with the initial HbA1c level. Accordingly, in this particular example, the chromium dosages would be as follows: for a patient having an HbA1c level in the range of about 7 up to about 8, a dose of chromium is in the range of about 0.003 mg Cr or less kg of body weight up to about 0.009 mg Cr or less/kg, for a patient having an HbA1c level in the range of about 8 up to about 9, a dose of chromium is in the range of about 0.005 mg Cr/kg of body weight up to about 0.01 mg Cr/kg of body weight, for a patient having an HbA1c level in the range of about 10 up to about 11, a dose of chromium is in the range of about 0.006 mg Cr/kg of body weight up to about 0.015 mg Cr/kg of body weight, and for a patient having an HbA1c level in the range of at least about 11, a dose of chromium in the range of about 0.007 mg Cr/kg of body weight up to about 0.04 mg Cr or more/kg of body weight. The particular dose of chromium would be maintained for a trial period, whereupon the HbA1c level would be measured again. If the patient's HbA1c level had dropped during the trial period, then the dose of chromium ingested could be reduced; if the HbA1c level had not decreased, the patient would have a number of options: the dose of chromium could be increased, the same dose could be ingested for a longer time period, or a different chromium complex with potentially differing bioavailability and potency for the particular individual could be used. This program could be applied to any other component or ingredient of the present invention, including, for example, any vanadium containing complex.

In addition to those indices already discussed above, a number of parameters of blood serum may be measured to assess the efficacy of any supplement or method of the present invention in attending to the conditions described herein. Any of these parameters may serve as the basis of a program of the present invention. Useful parameters include: LDL-cholesterol, HDL-cholesterol, apolipoprotein A1, apolipoprotein B, HbA1c, and blood sugar level (fasting, post-prandial and urine). It has been observed that the subject compositions are especially effective in improving blood glucose control after eating, so the post-prandial measurement may be preferred in certain embodiments of the present invention.

Other measurements of import for any subject invention include heart rate, blood pressure, weight, and temperature. To assess the present invention's affect on a patient's body condition, the following may be monitored: various skin-fold thicknesses, bicep and calf circumferences, body weight, lean body mass, percent body fat, body mass index (BMI), and waist-to-hip ratio (WHP).

The amounts of the individual components of preparations of this invention may vary, although in certain preparations the components are present in amounts lying within certain ranges presented herein. The present invention typically contemplates administering the dosages of any supplement or composition on a daily basis, or at other frequencies appropriate to the supplement or composition and its mode of delivery. For example, a dose of a composition of the present invention may be ingested or administered daily in a single serving, e.g., a tablet or a liquid, or in multiple servings. Alternatively, the dosages of the present invention may be ingested over a several day period or over any other time period so as to achieve the desired therapeutic effects.

Certain supplements and compositions of the present invention contemplate components that are transition metal chelates. Certain of the metal chelates contemplated by the present invention may have, in addition to any chelating ligand or ligands that are bound covalently or through ionic interactions to said metal ion, a counter-ion that is generally not bound to the metal ion (or if associated, only weakly so), and counters any charge of the metal-ligand complex. For example, in vanadyl sulfate hydrate, the sulfate would generally be considered a counter-ion to the vanadyl ion metal-ligand complex. Some examples of commonly encountered counter-ions include sulfate, perchlorate, nitrate, halogens, and the like. In addition, the metal chelates may have a number of waters of hydration associated with them. For example, one form of magnesium dichloride is magnesium dichloride hexahydrate, in which six waters of hydration are part of the metal complex. A metal chelate that is identified as an hydrate may have one or more waters of hydration. In addition, the number of molecules of waters of hydration may be a non-integer number when expressed as a ratio of one molecule of metal complex to the molecular number of the waters of hydration.

In providing a dose of transition metal chelate to a subject, the most appropriate dose may depend, in part, on the nature of the metal chelate. Certain transition metal or mono- or multi-valent ion complexes may be more readily assimilated than others, and may therefore be more effective in achieving the desired therapeutic response than other complexes. Another important factor may be the water solubility of any metal complex. Another relevant factor maybe the mode of administration. Consequently, dosages of the complexes typically contemplated by the present invention usually depend on the identity of the complex, the means of administration, and the formulation in which the complex is administered.

For instance, chromium picolinate appears to be absorbed at a rate about four times greater than chromium trichloride upon oral administration to rats. Usually, a chromium picolinate is preferred over chromium trichloride as the administered complex. In other embodiments, chromium polynicotinate will be preferred over chromium picolinate as it contemplated that chromium polynicotinate will generally have better absorption and metabolic properties than chromium picolinate.

For many transition metal chelates (or other metal chelates), such as those contemplated by the present invention, the metal chelate or other inorganic complex administered to a subject may differ from the form that is responsible for any biological activity. Furthermore, many different complexes of the same transition metal may cause a biological response to different degrees. For instance, a transition metal complex may undergo any number of reactions in vivo, including: hydrolysis, which depends greatly on pH conditions; redox reactions, whereby the transition metal, or even a chelating ligand, may change electronic state, which depends greatly on the local redox environment; and other ligation reactions, whereby a molecule may, because of, for example, superior binding characteristics and/or affinity or greater concentration, displace a ligand chelating the metal. It is not uncommon for a transition metal complex, especially those containing first row transition metals, to undergo complete hydrolysis upon ingestion or administration to a subject and possibly chelation by a molecule present in vivo. Generally, complexed forms of such metals will be selected to direct or maintain the desired form of the metal in the body. Other potentially desirable characteristics in metal complexes include: a neutral charge to the complex, sufficient water solubility (e.g., capable of forming an at least a 0.1 mM solution); and capable of being absorbed orally and gastro-intestinally.

For the different transition metals that serve as components in the subject supplements, particular complexes are discussed in more detail herein. In addition, acceptable salts of such transition metals that may serve as components in the subject preparations generally include the conventional non-toxic salts of the compounds, e.g., salts derived from non-toxic organic or inorganic acids. For example, such conventional non-toxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, valeric, oleaic, lauric, lactic, lactobionic, laurylsulphic, and the like. See, for example, Berge et al. *J. Pharm. Sci.* 66:1–19 (1977). For the different transition metal or other metal complexes of the present invention described herein, the dosages are presented with reference to the amount of elemental transition metal or other metal in such complex, unless otherwise expressly indicated or implied by the context.

Contemplated equivalents of the components of the subject compositions of the present invention include compounds or materials that otherwise correspond thereto, and which have the same general properties thereof, wherein one or more simple variations of substituents are made which do not adversely affect the efficacy of the compound in the composition or in use in the contemplated method.

As explained herein in greater detail, the invention will readily enable the design and implementation of trials in warm-blooded animals, including humans and mammals, necessary for easily determining or tailoring the form and dose for any supplement, and the components thereof, of the present invention.

3. Exemplary Compositions and Methods of Using the Same

The present invention provides in part for dietary supplements or compositions that enhance glucose metabolism. In certain embodiments, one or more of the components of the subject composition may be responsible for such enhancement. Preferably, embodiments of the invention include supplements or compositions that enhance glucose metabolism, while treating or reducing the severity of many of the secondary or risk factors that often accompany diabetes or IGT. Although the subject supplements or compositions may be used by individuals with no apparent symptoms of diabetes, the supplement is particularly suited for use by individuals with IGT and/or diabetes to prevent, reduce or eliminate the necessity of using insulin. The present invention also contemplates using the formulations in conjunction with other methods of treating diabetic and pre-diabetic individuals, or otherwise reducing the severity of their condition. For example, the formulations of the present invention may contain other ingredients such as anti-diabetic agents that work with insulin to enhance the effect of insulin on the regulation of glucose concentration in the blood by improving metabolism of glucose in the insulin sensitive cells of the body.

Without limiting the invention to a particular mechanism of action, both chromium and vanadium may act at two different levels in the body: 1) gastrointestinal tract activity, particularly localized to the intestine; and 2) systemic activity. These two levels of action are at the organ level and include additional effects at the cellular and subcellular level.

In the gastrointestinal tract, chromium and vanadium (either individually, or preferably in concert) modulate sugar transport (e.g., glucose transport) by typically slowing glucose absorption. Slower glucose absorption slows insulin release and reduces excessive insulin responses in response to rising blood glucose levels after a meal. This benefits pancreatic secretion of insulin by reducing both the glucose load and rate of glucose load over the initial phases of glucose detection, absorption and metabolism by the body. Reduced rates of glucose loading reduces the stress on beta cells normally associated with the insulin response to rising glucose.

Moreover, slower or modulated glucose absorption permits more time for insulin to stimulate normal sugar metabolic routes either before glucose loading is complete, or during a slower rate of glucose loading. Consequently, insulin dependent mechanisms have more time to prepare for the arrival of sugars from the intestine. This modulation of glucose absorption improves short-term insulin modulation in the liver, muscle, and adipose tissue. These effects in the gastrointestinal tract are, in all likelihood, short-term responses, and they are not necessarily associated with the longer-term systemic effects of chromium and vanadium administration.

In addition, chromium and vanadium may potentially slow glucose metabolism by interacting with the intestine, particularly the epithelium of the intestine responsible for sugar metabolism (including absorption). One primary mechanism for sugar transport in the gut is sodium facilitated sugar transport. Such transporters are located in the lumenal membrane of the epithelium. The basolateral membrane may also have an additional sugar transporter that facilitates transport out the cell and into the blood. For net sugar absorption from the lumen of the gut to the blood, sodium facilitated sugar transport generally requires a sodium concentration favorable to the diffusion of sodium into the epithelium cell from the lumen. This concentration gradient is largely generated by the active transport of the Na/K ATPase in the epithelium cells, which generally transports three sodium atoms out of the cell to the blood side of the epithelium in exchange for two sodium atoms in the reverse direction.

Each cycle of the pump requires hydrolysis of one ATP to transport sodium and potassium against their respective concentration gradients. The hydrolysis reaction requires a divalent cation, typically magnesium. In many instances, however other divalent cations may substitute or enter into the hydrolysis reaction with varying degrees of catalytic activity or inhibition. Substitution of trivalent cations for divalent cations in the cycle generally leads to significant inhibition of the pumping activity and/or dephosphorylation from the phosphoenzyme intermediate state. Chromium may thus inhibit the Na/K ATPase activity by substituting for magnesium and thereby inhibiting relative to magnesium catalytic and transport activity giving rise to a decreased sodium gradient across the lumenal membrane. The reduced gradient effects sugar transport by reducing the thermodynamic and kinetic forces favoring sugar entry from the gut.

In addition, during the hydrolysis of ATP in the catalytic cycle of the Na/K ATPase, a phosphoenzyme intermediate (EP) is formed between phosphate and an aspartic acid at the active site of APTase. This covalent EP is transient and is chemical distinct from phosphorylated proteins associated with kinases and phosphatases, which have also been shown to be affected by vanadium. Formation of EP in the catalytic cycle for Na/K ATPase is inhibited by vanadate present at low concentrations of less than 1 micromolar. Vanadate binds to the active site as a transition state analog of phosphate in a vanadyl-enzyme, or EV complex, rather than EP. The EV complex is highly stable, as vanadate the kinetics of loss of vanadate from the EV complex is relatively slow. Vanadate may thus effectively inhibit the Na/K ATPase by disrupting catalysis through the formation of EV giving rise to a decreased sodium gradient across the lumenal membrane. Consequently, the reduced gradient reduces sugar entry from the intestine.

Chromium and vanadium also operate at the systemic level after absorption of the two transition metals from the gut. Major sites of activity include the liver, muscle and adipose tissue. Vanadium may have particular activity with respect to phosphorylation systems, including the many phosphorylated proteins responsible for modulating metabolism. Chromium may also modulate metabolism at the cellular level. These systemic effects generally improve the action of insulin and/or metabolic pathways associated with sugar and/or lipid metabolism.

The dosing for chromium and vanadium components in the subject compositions and methods may depend in part on the mechanisms of action discussed above. Both chromium and vanadium may be stored in long term (e.g., about 2 to 6 weeks) compartments which may provide diffusable sites of chromium and vanadium for maintaining elevated levels of chromium and vanadium in a patient. In treatment, it may be possible to load such sites with chromium or vanadium and then taper or abate the dose of the transition metals over time to allow the deposits to be reduced. The deposit sites may then be reloaded and the tapering repeated as necessary.

In certain embodiments of the invention, it may be desirable to tailor dosing of chromium and vanadium to the (as well as other components described herein) caloric intake. By combining ingestion of chromium or vanadium with caloric intake, for instance, more desirable absorption and metabolic patterns of caloric sources, particularly sugars, may be achieved. The short-term effects attributable to chromium and vanadium may, in particular, beneficially modulate absorption and metabolism.

In regard to absorption and metabolism of the subject compositions, and the different components thereof, features of the alimentary tract may affect how compositions of the present invention, and methods of using the same, are utilized when ingested orally. The elements of the alimentary tract, including the gastrointestinal tract, may affect the dosage required for any such modality. Such features are well known to those of skill in the art.

3.1 Anti-Diabetic Agents

Current drugs or anti-diabetic agents used for managing diabetes and its precursor syndromes, such as insulin resistance, that are well-known in the art fall within five classes of compounds: the biguanides, thiazolidinediones, the sulfonylureas, benzoic acid derivatives and glucosidase inhibitors. The biguanides, e.g., metformin, are believed to prevent excessive hepatic gluconeogenesis. The thiazolidinediones are believed to act by increasing the rate of peripheral glucose disposal. The sulfonylureas, e.g., tolbutamide and glyburide, and the benzoic acid derivatives, e.g. repaglinide, lower plasma glucose by stimulating insulin secretion.

In addition to these agents, a number of other therapies may be used in combination with the supplements of the present invention to improve glucose control. Certain of these anti-diabetic agents have not yet been approved for human use.

Among biguanides useful as diabetic therapeutic agents, metformin has proven particularly successful. Metformin (N,N-dimethylimidodicarbonimidicdiamide; 1,1-dimethylbiguanide; N,N-dimethylbiguanide; N,N-dimethyldiguanide; N'-dimethylguanylguanidine) is an anti-diabetic agent that acts by reducing glucose production by the liver and by decreasing intestinal absorption of glucose. It is also believed to improve the insulin sensitivity of tissues elsewhere in the body (increases peripheral glucose uptake and utilization). Metformin improves glucose tolerance in impaired glucose tolerant (IGT) subjects and Type 2 diabetic subjects, lowering both pre- and post-prandial plasma glucose. Metformin is generally not effective in the absence of insulin. Bailey, *Diabetes Care* 15:755–72 (1992).

Unlike other agents for treating diabetes, such as the sulfonylureas, metformin does not appear to produce hypoglycemia in either diabetic or non-diabetic subjects. With metformin therapy, insulin secretion remains unchanged while fasting insulin levels and day-long plasma insulin response may decrease. The efficacy of metformin has been shown in several trials. In one study of moderately obese Type 2 diabetics, HbA1c levels improved from 8.6% to 7.1% after 29 weeks of metformin therapy alone or in combination with sulfonylurea. DeFronzo et al., *New Engl. J. Med.* 333:541–49 (1995). Metformin also had a favorable effect on serum lipids, lowering mean fasting serum triglycerides, total cholesterol, and LDL cholesterol levels and showing no adverse effects on other lipid levels. In another trial, metformin improved glycemic control in NIDDM subjects in a dose-related manner. After 14 weeks, metformin 500 and 2000 mg daily reduced HbA1c by 0.9% and 2.0%, respectively. Garber et al., *Am J. Med.* 102:491–97 (1997).

Metformin may have a beneficial therapeutic effect on insulin resistant non-diabetics. One study indicated that treatment of hypertensive obese non-diabetic women with metformin decreased blood pressure, fasting and glucose-stimulated plasma insulin fibrinogen. Giugliano et al., *Diabetes Care* 16:1387–90 (1993).

Metformin is commonly administered as metformin HCl. This as well as all other useful forms of metformin are contemplated for use in the practice of the present invention. Generally, a fixed dosage regimen is individualized for the management of hyperglycemia in diabetes with metformin HCl or any other pharmacologic agent. Individualization of dosage is made on the basis of both effectiveness and tolerance, while generally not exceeding the maximum recommended daily dose of 2550 mg. In one embodiment of the present invention, compositions comprise in the range of about 10 mg up to about 2550 mg per daily dose. Many patients observe benefits at 500 mg per day. In some embodiments of the invention, dosages may be less than 1000 mg per day when administered with the other components of any supplement of the present invention. Some subject experience gastrointestinal side effects, which may be alleviated by dosage reduction. A rare but severe side effect of metformin therapy is lactic acidosis.

In combination therapy, metformin is often used with sulfonylureas, alpha-glucosidase inhibitors, troglitazeon, and insulin. Metformin combined with a sulfonylurea increases insulin sensitivity and may lower plasma glucose. Alternatively, metformin with repaglinide may be more effective than glipizide, and at least as effective as glyburide, in maintaining glycemic control over many months. Metformin with troglitazone improves glucose control in excess of either agent alone. Inzucchi et al., *New. Eng. J. Med.* 338:867–72 (1998).

Thiazolidinediones contemplated for use in the practice of the present invention include troglitazone, and the like. Such compounds are well-known, e.g., as described in U.S. Pat. Nos. 5,223,522, 5,132,317, 5,120,754, 5,061,717, 4,897,405, 4,873,255, 4,687,777, 4,572,912, 4,287,200, and 5,002,953; and *Current Pharmaceutical Design* 2:85–101 (1996). Troglitazone is an oral antihyperglycemic agent that increases glucose transport possibly by activation of peroxisome proliferator-activated receptor-γ (PPARγ). By such activation, troglitazone enhances expression of GLUT4 glucose transporters, resulting in increased insulin-stimulated glucose uptake. Troglitazone may also attenuate gluconeogenesis and/or activation of glycolysis.

Glycemic control resulting from troglitazone therapy reduces HbA1c by approximately 1 to 2%. Mimura et al., *Diabetes Med.* 11:685–91 (1994); Kumar et al., *Diabetologia* 39:701–09 (1996). Effects may not occur for a few weeks after beginning therapy. Troglitazone may also decrease insulin requirements. In one trial of patients with NIDDM and using exogenous insulin, mean HbA1c fell by 0.8% and 1.4% for doses of 200 and 600 mg troglitazone, respectively. Insulin requirements were reduced by up to 29%. Schwartz et al., *New Engl. J. Med.* 338:861–66 (1998). In another study of NIDDM diabetics using 400 and 600 mg troglitazone, fasting and post-prandial glucose levels were decreased, and hyperinsulinemic euglycemic clam indicated that glucose disposal was approximately 45% above pretreatment levels. Maggs et al., *Ann. Intern. Med.* 128:176–85 (1998). For all these studies, triglyceride concentrations are lowered and HDL increased, whereas LDL may or may not be increased. Troglitazone does not appear to cause hypoglycemia during monotherapy, but it may result when troglitazone is used in combination with insulin or a sulfonylurea.

Troglitazone may be used to delay or prevent Type 2 diabetes in certain embodiments of the present invention. In one study, 400 mg of troglitazone increased glucose disposal rates in obese patients with either impaired or normal glucose tolerance. Nolan et al., *New. Eng. J. Med* 331:1188–93 (1994). In another study of women with IGT and a history of gestational diabetes, 600 mg troglitazone improved insulin homeostasis, including improving insulin sensitivity and lowering circulating insulin concentrations, but glucose tolerance was unchanged. Berkowitz et al., *Diabetes* 45:172–79 (1996). Thiazolidinediones may be used with at-risk populations for NIDDM, such as women with POCS or GDM, to prevent or delay the onset of NIDDM. U.S. Pat. No. 5,874,454.

Effective amounts of troglitazone, when used alone, range from about 10 mg up to about 800 mg per daily dose and a commensurate range is contemplated for use in the present invention. In certain aspects of the present invention, the composition comprises from about 100 mg to about 600 mg of troglitazone per daily dose, or alternatively 400 mg. The daily dose may subdivided for administration on two, three, or more occasions during the day.

In addition to being used with metformin, troglitazone may be used in combination with insulin and a sulfonylurea agent. See, for example, U.S. Pat. No. 5,859,037.

In the present invention, sulfonylureas may be used to treat diabetes. Sulfonylureas generally operate by lowering plasma glucose by increasing the release of insulin from the pancreas. Specifically, sulfonylureas act by blocking the ATP-sensitive potassium channels. The sulfonylurea glimepiride may also increase insulin sensitivity by stimulating translocation of GLUT4 transporters. Sulfonylureas are typically prescribed when HbA1c is above 8%. See also U.S. Pat. Nos. 5,258,185, 4,873,080.

The sulfonylureas are a class of compounds that are well-known in the art, e.g., as described in U.S. Pat. Nos. 3,454,635, 3,669,966, 2,968,158, 3,501,495, 3,708,486, 3,668,215, 3,654,357, and 3,097,242. Exemplary sulfonylureas contemplated for use in certain embodiments of the present invention (with typical daily dosages indicated in parentheses) include acetohexamide (in the range of about 250 up to about 1500 mg), chlorpropamide (in the range of about 100 up to about 500 mg), tolazimide (in the range of about 100 up to about 1000 mg), tolbutamide (in the range of about 500 up to about 3000 mg), gliclazide (in the range of about 80 up to about 320 mg), glipizide (in the range of about 5 up to about 40 mg), glipizide GITS (in the range of about 5 up to about 20 mg), glyburide (in the range of about 1 up to about 20 mg), micronized glyburide (in the range of about 0.75 up to about 12 mg), glimeperide (in the range of about I up to about 8 mg), AG-EE 623 ZW, and the like. Glimepiride is the first anti-diabetic agent in this class to be approved for use with insulin, and there may be less risk of hypoglycemia associated with its use.

A variety of alpha-glucosidase inhibitors may used in certain embodiments of the present invention to treat and/or prevent diabetes. Such inhibitors competitively inhibit alpha-glucosidase, which metabolizes carbohydrates, thereby delaying carbohydrate absorption and attenuating post-prandial hyperglycemia. Clissod et al., *Drugs* 35:214–23 (1988). These decrease in glucose allows the production of insulin to be more regular, and as a result, serum concentrations of insulin are decreased as are HbA1c levels. There does not appear to be any increased insulin sensitivity, however.

Exemplary alpha-glucosidase inhibitors contemplated for use in the practice of the present invention include acarbose, miglitol, and the like. Effective dosages of both acarbose and miglitol are in the range of about 25 up to about 300 mg daily.

Alpha-glucosidase inhibitors may be used in combination with sulfonylureas, and they appear to be about on-half as effective as sulfonylureas or metformin in reducing glucose levels. HbA1c levels generally decrease from 0.5 to 1.0%. In addition, alpha-glucosidase inhibitors have been shown to be effective in reducing the post-prandial rise in blood glucose. Lefevre et al., *Drugs* 44:29–38 (1992).

A variety of benzoic acid derivatives may used in certain embodiments of the present invention to treat and/or prevent diabetes. These agents, also known as meglitinides, are non-sulfonylurea hypoglycemic agents having insulin secretory capacity. For example, repaglinidc appears to bind to ATP-sensitive potassium channels on pancreatic beta cells and thereby increases insulin secretion. Exemplary benzoic acid derivatives contemplated for use in the practice of the present invention include repaglinide and the like. For repaglinide, the effective daily dosage may be in the range of about 0.5 mg up to about 16 mg, and the agent may be taken before each meal.

In another illustrative embodiment, the subject supplements may be conjointly administered with a an M1 receptor antagonist. Cholinergic agents are potent modulators of insulin release that act via muscarinic receptors. Moreover, the use of such agents can have the added benefit of decreasing cholesterol levels, while increasing HDL levels. Suitable muscarinic receptor antagonists include substances that directly or indirectly block activation of muscarinic cholinergic receptors. Preferably, such substances are selective (or are used in amounts that promote such selectivity) for the M1 receptor. Nonlimiting examples include quaternary amines (such as methantheline, ipratropium, and propantheline), tertiary amines (e.g. dicyclomine, scopolamine) and tricyclic amines (e.g. telenzepine). Pirenzepine and methyl scopolamine are preferred. Other suitable muscarinic receptor antagonists include benztropine (commercially available as COGENTIN from Merck), hexahydro-sila-difenidol hydrochloride (HHSID hydrochloride disclosed in Lambrecht et al., *Trends in Pharmacol. Sci.* 10(Suppl):60 (1989); (+/−)-3-quinuclidinyl xanthene-9-carboxylate hemioxalate (QNX-hemioxalate; Birdsall et al., *Trends in Pharmacol. Sci.* 4:459 (1983); telenzepine dihydrochloride (Coruzzi et al., *Arch. Int. Pharmacodyn. Ther.* 302:232 (1989); and Kawashima et al., *Gen. Pharmacol.* 21:17 (1990)) and atropine. The dosages of such muscarinic receptor antagonists will be generally subject to optimization as outlined below. In the case of lipid metabolism disorders, dosage optimization may be necessary independently of whether administration is timed by reference to the lipid metabolism responsiveness window or not.

In terms of regulating insulin and lipid metabolism and reducing the foregoing disorders, the subject formulations or supplements may also act synergistically with prolactin inhibitors such as d2 dopamine agonists (e.g. bromocriptine). Accordingly, the subject method may include the conjoint administration of such prolactin inhibitors as prolactin-inhibiting ergo alkaloids and prolactin-inhibiting dopamine agonists. Examples of suitable agents include 2-bromo-alpha-ergocriptine, 6-methyl-8 beta-carbobenzyloxyaminoethyl-10-alpha-ergoline, 8-acylaminoergolines, 6-methyl-8-alpha-(N-acyl)amino-9-ergoline, 6-methyl-8-alpha-(N-phenylacetyl)amino-9-ergoline, ergocomine, 9, 10-dihydroergocornine, D-2-halo-6-alkyl-8-substituted ergolines, D-2-bromo-6-methyl-8-cyanomethylergoline, carbidopa, benserazide and other dopadecarboxylase inhibitors, L-dopa, dopamine and non toxic salts thereof. Methods of administering prolactin inhibitors have been devised to minimize the reduction in metabolic rate which may result from such therapy. U.S. Pat. Nos. 5,866,584; 5,744,477.

A number of agents are presently under investigation as potential anti-diabetics in humans. Any of such agents may be used in the present invention for treatment and/or prevention of diabetes if they become available for therapeutic use.

Another category of anti-diabetic agents that is still undergoing safety and efficacy trials is inhibitors of carnitine palmitoyl-transferase I (CPT-I), such as etomoxir. Subject to its approval for human use, etomoxir and other like agents may be used in certain embodiments of the present invention. Etomoxir irreversibly inhibits carnitine palmitoyl-transferase I, which is necessary for fatty acid oxidation. Such inhibition may reducde fasting hyperglycemia, because products of fatty acid oxidation stimulate hepatic gluconeogenesis. Etomoxir may improve insulin sensitivity in Type 2 diabetics. Hubinger et al., *Hormone Metab. Res.* 24:115–18 (1992). Although early CPT-1 inhibitors caused cardiac hypertrophy in animals, newer inhibitors such as etomoxir may show less cardiotoxicity.

Another class of anti-diabetic agents that, subject to the necessary regulatory approval(s), may be used in certain embodiments of the present invention, are amylin compounds. Amylin is a 37 amino acid polypeptide synthesized and secreted along with insulin from beta cells. Early studies indicate that such compounds reduce post-prandial increases in serum glucose.

Still other anti-diabetic agents that may be used in certain embodiments of the present invention are dipeptidyl peptidase IV inhibitors and glucagon-like polypeptides (I) (glp 1), (glp2), or other diabetogenic peptide hormones.

3.2 Components of Compositions or Supplements

In certain embodiments, the compositions of the present invention may augment or supplant other forms of diabetes and IGT treatment, such as insulin. In certain embodiments, programs of the present invention require that the subject compliment such treatment methods with the compositions of the present invention.

In one embodiment of the present invention, it has been discovered that a composition containing an anti-diabetic agent and the following components in effective amounts and metabolically available forms: vanadium, chromium, magnesium, and vitamin E in combination with naturally available sources of aspirin, alpha-lipoic acid, and folic acid, improves the metabolism of glucose. Such compositions may be also used to arrest, treat or otherwise reduce the severity of many of the cardiovascular complications or risk factors associated with diabetes or pre-diabetes. These components perform different functions which, when administered in appropriate dosages and forms, typically enhance the metabolism of glucose In part, the present invention contemplates combinations of anti-diabetic agents and components in different supplements or compositions to produce a therapeutic effect in a patient with a glucose metabolism disorder, such as Type 2 diabetes, IGT, Syndrome X, insulin resistance, or hyperinsulinemia. In general, the therapeutic effect may be measured by reference to any number of indices that are directly related to glucose metabolism, such as blood glucose level or HbA1c level, or other parameters that may otherwise be affected by such a disorder or a related condition or disease. The present invention teaches how to test supplements or compositions containing any one or more of the components set forth herein to determine whether any particular combination of anti-diabetic agents and components in a supplement or composition results in a desirable therapeutic effect upon administration to a patient.

In certain embodiments, the subject compositions contain, in addition to an anti-diabetic agent, at least a therapeutically effective amount of a bioavailable source of chromium. In other embodiments, the subject compositions contain, in addition to an anti-diabetic agent, at least a therapeutically effective amount of a bioavailable source of vanadium. In still other embodiments, the present invention includes, in addition to an anti-diabetic agent, both bioavailable sources of chromium and vanadium.

3.2.1 Chromium

Chromium is a trace mineral found in human tissues. Claims surrounding the use of chromium as a supplement, such as weight loss and building muscle mass, have been made for non-diabetic individuals. Notwithstanding such claims, the status of chromium supplementation, even for diabetic patients, appears to be unsettled. Although chromium supplementation may be prescribed for individuals who are chromium deficient, the prevalence of chromium deficiency in diabetic patients appears to be difficult to establish.

Without limiting the invention to a particular mechanism of action, chromium at the appropriate dosage and form may cause improved glucose or lipid metabolism by overcoming insulin resistance. Chromium may increase insulin binding to cells by increasing the number of insulin receptors. Alternatively, chromium may increase insulin sensitivity by increasing insulin receptor phosphorylation.

The present invention contemplates metal complex of chromium in which the chromium is bioavailable. Some examples of such sources of chromium include chromium trichloride, chromium acetate, chromium nicotinate (or polynicotinate), chromium picolinate, chromium glycinate, chromium oxalate, chromium perchlorate, chromium salicylate, chromium nicotinate glycinate, chromium 4oxo-pyridine-2,6-dicarboxylate, chromium chelidamate or arginate; and chromium tris-acetylacetonate. Another possible source of chromium is glucose tolerance factor, which contains chromium thought to be complexed as chromium nicotinate. Finally, in addition to those metal complexes specifically set forth herein, other salts and complexes of chromium known to those of skill in the art are contemplated by the present invention. As discussed generally above, the chromium complexes contemplated by the present invention may differ in bioavailability and potency.

The chromium complexes may contain chromium in the (III) (i.e., trivalent), (VI) (i.e., hexavalent), or other valent states, although it is believed that the trivalent state is responsible for biological effects of interest in the present invention and is therefore preferred. Chromium in many of the chromium containing complexes contemplated by the present invention typically have chromium in the (Ill) valency.

Certain embodiments of the present invention contemplate doses of chromium from about 100 mcg to about 5000 mcg or higher. Unless expressly provided otherwise, the dose amounts referred to herein refer to the amount of chromium in any particular form, such as complex or in any particular valency. By way of example, to provide 200 mcg of chromium using chromium trichloride, a patient would need to ingest about 610 mcg of chromium trichloride.

Particular dosages of chromium contemplated by the present invention include about 200 mcg, 300 mcg, 333 mcg, 500 mcg, 650 mcg, 750 mcg, 1000 mcg, 1250 mcg, 1500 mcg, 2000 mcg, 2500 mcg, 3000 mcg, 3500 mcg, 4500 mcg, and 5000 mcg, as well as other possible dosages determined by one of skill in the art. Higher dosages, while they may be daily dosages, may be used as short term regimes (e.g. less than about one month) and may taper into dosages in the lower end of the taught ranges. In certain instances, it may be advantageous not to fall below about 250 to 600 mcg of chromium per day when tapering the dose.

In certain embodiments, the dose of chromium may be modified if the supplement or composition contains a bioavailable source of vanadium. For example, the dose of chromium may be reduced by from about 10% to about 75%, or alternatively 25%, 33%, 55%, or 66%. The amount of reduction in the chromium dose may depend, in part, on the dose of vanadium provided for in any supplement of the present invention, as well as the source of the vanadium and the means of administration.

For any of the components described herein, the dose may be varied as necessary, for example, to treat one or more specific conditions set forth herein, or for example, to reflect any differences in administration or the nature of the components employed in any particular composition, method or program of the present invention. For example, the dose of chromium may be reduced as ingestion of the supplement results in improved blood glucose control. The patient may need to monitor a number of indices, such as blood glucose levels or HbA1c levels, to determine the appropriate dosing.

In additional embodiments of present invention, the dose of chromium is based on the weight of the intended recipient. Accordingly, in one embodiment of the present invention, the dose of chromium is in the range of about 0.001 mg or less/kg of body weight up to about 0.06 mg or more/kg of body weight. In another embodiment of the present invention, the dose is at least about 0.01 mg/kg body weight. In still another embodiment of the present invention, the dose is in the range of about 0.002 mg/kg of body weight up to about 0.02 mg/kg of body weight.

In further embodiments of the present invention, the dose of chromium may be determined based on the intended recipient's condition. For example, in one embodiment, the dose of chromium may depend on the subject's HbA1c level. Accordingly, in this particular example, for a patient having an HbA1c level in the range of about 7 up to about 8, a dose of chromium is in the range of about 0.003 mg or less/kg of body weight up to about 0.009 mg or less/kg, for a patient having an HbA1c level in the range of about 8 up to about 9, a dose of chromium is in the range of about 0.005 mg/kg of body weight up to about 0.01 mg/kg of body weight, for a patient having an HbA1c level in the range of about 10 up to about 11, a dose of chromium is in the range of about 0.006 mg/kg of body weight up to about 0.015 mg/kg of body weight, and for a patient having an HbA1c level in the range of at least about 11, a dose of chromium in the range of about 0.007 mg/kg of body weight up to about 0.04 mg or more/kg of body weight. Dosing for a particular's subject condition may be based on any of the parameters known in the art or described herein useful for assessing the condition of any subject. For example, a number of parameters of blood serum, in addition to HbA1c levels, may be used to determine appropriate dosing. Other measurements of import of potential use for dosing purposes are described herein.

Chromium in the trivalent state is one of the least toxic nutrients: the reference dose established by the US EPA is 350 times the upper limit of the Estimated Safe and Adequate Daily Dietary Intake (ESADDI) of 200 mcg per day, wherein the reference dose is defined as the estimate (with uncertainty spanning perhaps an order of magnitude) of a daily exposure to a human population, including sensitive subgroups, that is likely to be without appreciable risk of deleterious effects over a lifetime. Consequently, the present invention contemplates doses of trivalent chromium that substantially surpass the ESADDI but which may be necessary to produce the greatest therapeutic effect.

3.2.2 Vanadium

In sonic embodiments, vanadium compounds of the present invention are believed to have an insulin mimetic effect. Vanadium, often in the form of vanadate appears in certain tissues to stimulate glucose transport activate glycogen synthase, increase glycogen syntheses in fat cells, and stimulate carbohydrate uptake in the liver like insulin.

A commonly used source of vanadate is vanadyl sulfate. Upon ingestion, vanadyl sulfate is typically reduced to vanadate, which is a salt, of vanadic acid. Glycogen synthase is an enzyme that causes the conversion of glucose into glycogen. Vanadate appears to activate glycogen synthase in the same manner as insulin. For example, vanadate appears to have no effect if insulin concentration is at a maximum, whereas if insulin is at less than maximum, vanadate increases both glycogen synthase activation state and 2-deoxyglucose transport to the level obtained if insulin were at maximized. Vanadate and insulin activate glycogen synthase within similar time frames, and adrenaline partially reverses both vanadate and insulin activated glycogen synthase. Also, insulin and vanadate counteract the activating effect of adrenaline on glycogen phosphorylase.

Dosages of vanadium in compositions of the present invention range from less than 5 mg to more than 100 mg. Unless expressly provided otherwise, the dose amounts referred to herein refer to the amount of vanadium in any particular form, such as any particular complex or in any particular valency.

Particular dosages of vanadium contemplated by the present invention include about 0.1 mg, 1 mg, 5 mg, 10 mg, 20 mg, 25 mg, 50 mg, 75 mg, 100 mg, and 125 mg. In certain embodiments, the amount of vanadium administered is about 5 mg to 50 mg. Typically, these are daily dosages. Higher dosages, while they may be daily dosages, may be used as short term regimes (e.g. less than about one month) and may taper into dosages in the lower end of the taught ranges.

In certain embodiments, it may be useful to represent the preceding doses may be in terms of vanadyl ($VO^{2+}$) instead of vanadium. Such dosages would be: 0.1 mg V, 0.13 mg $VO^{2+}$; 1 mg V, 1.3 mg $VO^{2+}$; 5 mg V, 6.55 mg $VO^{2+}$; 10 mg V, 13.1 mg $VO^{2+}$; 20 mg V, 26.2 mg $VO^{2+}$; 25 mg V, 32.8 mg $VO^{2+}$; 50 mg V; 65.5 mg $VO^{2+}$; 75 mg V, 98.3 mg $VO^{2+}$; 100 mg V, 131 mg $VO^{2+}$; and 125 mg V, 164 mg $VO^{2+}$.

In certain embodiments, the compositions of the present invention include vanadyl sulfate hydrate as a vanadium source. In one such embodiment, the amount of elemental vanadium in the source of vanadium sulfate hydrate was determined by elemental analysis to be approximately 20% by weight, which corresponds to about five to six waters of hydration per molecule of vanadyl sulfate. For any embodiment using such a source of vanadyl sulfate hydrate, some of the common doses of vanadium and the resulting amount of vanadyl sulfate hydrate necessary to provide that amount of vanadium would be: 0.1 mg of vanadium, 0.5 mg of vanadyl sulfate hydrate; 20 mg of vanadium, 100 mg of vanadyl sulfate hydrate; 100 mg of vanadium, 500 mg of vanadyl sulfate hydrate.

In certain embodiments, the dose of vanadium may be modified if the supplement or composition contains a bioavailable source of chromium. For example, the dose of vanadium may be reduced by from about 10% to about 75%, or alternatively 25%, 33%, 55%, or 66%. The amount of reduction in the vanadium dose may depend, in part, on the dose of chromium provided for in any supplement of the present invention, as well as the source of the chromium and the means of administration.

For any of the components described herein, the dose may be varied as necessary, for example, to treat one or more specific conditions set forth herein, or for example, to reflect any differences in administration or the nature of the components employed in any particular composition, method or program of the present invention. For example, the dose of vanadium may be reduced as ingestion of the supplement results in improved blood glucose control. The patient may need to monitor a number of indices, such as blood glucose levels or HbA1c levels, to determine the appropriate dosing.

In additional embodiments of present invention, the dose of vanadium is based on the weight of the intended recipient. Accordingly, in one embodiment of the present invention, the dose of vanadium is in the range of about 0.1 mg or less/kg of body weight up to about 10 mg or more/kg of body weight. In another embodiment of the present invention, the dose is at least about 0.3 mg/kg body weight. In still another embodiment of the present invention, the dose is in the range of about 0.2 mg/kg of body weight up to about 0.8 mg/kg of body weight.

Alternatively, dosages based on the subject's weight may be based on the amount of vanadyl required in any embodiment of the present invention. Accordingly, in one embodiment of the present invention, the dose of vanadyl is in the range of about 0.13 mg or less kg of body weight up to about 13 mg or more/kg of body weight. In another embodiment of the present invention, the dose is at least about 0.42 mg/kg body weight. In still another embodiment of the present invention, the dose is in the range of about 0.26 mg/kg of body weight up to about 0.10 mg/kg of body weight.

In further embodiments of the present invention, the dose of vanadium may be determined based on the intended recipient's condition. For example, in one embodiment, the dose of vanadium may depend on the subject's HbA1c level. Accordingly, in this particular example, for a patient having an HbA1c level in the range of about 7 up to about 8, a dose of vanadium is in the range of about 0.05 mg or less/kg of body weight up to about 0.45 mg/kg; for a patient having an HbA1c level in the range of about 8 up to about 9, a dose of vanadium is in the range of about 0.15 mg/kg of body weight up to about 0.6 mg/kg of body weight, for a patient having an HbA1c level in the range of about 10 up to about 11, a dose of vanadium is in the range of about 0.3 mg/kg of body weight up to about 1.0 mg/kg of body weight, and for a patient having an HbA1c level in the range of at least about 11, a dose of vanadium in the range of about 0.35 mg/kg of body weight up to about 2.0 mg or more/kg of body weight. Dosing for a particular's subject condition may be based on any of the parameters known in the art or described herein useful for assessing the condition of any subject. For example, a number of parameters of blood serum, in addition to HbA1c levels, may be used to determine appropriate dosing. Other measurements of import of potential use for dosing purposes are described herein.

A number of vanadium containing compounds may be used in the present invention. For instance, vanadyl sulfate does not appear not to be associated with any apparent toxicity during treatment periods of up to one year. In addition, it appears that vanadyl sulfate may be less toxic than vanadate forms of vanadium. Other vanadium compounds contemplated by the present invention include any of the following: vanadium pentoxide; vanadium trisulfate; vanadyl chloride; vanadyl glycinate; vanadyl gluconate; vanadyl citrate; vanadyl lactate; vanadyl tartrate; vanadyl gluconate; vanadyl phosphate; sodium orthovanadate; vanadium chelidamate or arginate; and vanadyl complexes with monoprotic bidentate 2,4-diones. In addition to those vanadium complexes specifically set forth above, other organic, inorganic, salts and complexes of vanadium, including vanadyl complexes, known to those of skill in the art are contemplated by the present invention.

The different vanadium-containing metal complexes of the present invention may contain vanadium in any number of vanadium valencies. Vanadyl ion is $VO^{2+}$, which has vanadium in plus four oxidation state, is one form of vanadium that is preferred in supplements of the present invention.

3.2.3 Magnesium

Magnesium influences a broad diversity of functions in physiology and pathology. Magnesium is the second most abundant intracellular cation (positively charged element) in the body, predominately in muscle (skeletal and cardiac) and bone. It is required for to over 300 enzymatic reactions.

For instance, magnesium is essential for maintaining the activity of the sodium potassium adenine triphosphate (Na-K-ATPase) pump. Magnesium deficiency results in depletion of intracellular potassium (the most abundant intracellular cation) and sodium accumulation. In cardiac muscle, this electrolyte abnormality may cause electrocardiographic changes and cardiac irritability, leading to myocardial infarction and potentially lethal arrhythmias.

The recommended daily allowance of magnesium for humans is 350 mg. Magnesium in mammals typically resides in three compartments: (1) bone; (2) intracellular bound form or an intracellular unbound form; and (3) in circulating bound and unbound forms. When the concentration of circulating magnesium in the bloodstream increases as a result of the dietary intake of magnesium, the magnesium is sequestered into one of the bound or intracellular forms. Hypomagensium is generally defined as a serum magnesium level concentration of less than 1.5 mEq/l.

The incidence of magnesium deficiency in Type 1 and Type 2 diabetes appears to be unclear. The diabetic patient may be at risk for developing magnesium depletion via inadequate dietary intake and gastrointestinal and renal losses, especially with poorly controlled blood glucose and resultant glucosuria. However, the diagnosing magnesium deficiency in the clinical setting remains extremely difficult because serum magnesium measures only 0.3% of the total body magnesium and is therefore difficult to determine.

Magnesium, as used in the present invention, appears to improve glucose metabolism and to arrest or reduce any diabetes associated risk factors. Many preparations of magnesium are available but they may differ in potency, bioavailability (absorption), tolerability, and cost. Magnesium taken orally is absorbed primarily in the jejunum and ileum. Some magnesium salts, such as the oxide or the carbonate, although inexpensive, are not highly soluble in water, poorly absorbed and associated with gastrointestinal side effects, especially diarrhea. Other magnesium-containing complexes present better solubility, bioavailability, potency, tolerability, safety, and predictability in repleting intracellular and serum levels of magnesium.

Adjusting the dose as necessary for the particular magnesium complex employed, a number of magnesium containing complexes, or mixtures thereof, may be used in the subject preparations. Such molecules include: magnesium chloride; magnesium citrate; magnesium fumarate; magnesium succinate; magnesium orotate; magnesium aminodicarbonic acid fluoride, bromide and iodide; magnesium aspartate; magnesium stearate; magnesium glutamate; magnesium oxide; magnesium hydroxide; magnesium carbonate; magnesium hydrogen phosphate; magnesium glycerophosphate; magnesium trisilicate; magnesium hydroxide carbonate; magnesium acetate; magnesium citrate; magnesium gluconate; magnesium lactate; magnesium ascorbate; magnesium taurate; magnesium malate; and magnesium diglycinate.

It has been suggested that certain forms of magnesium are capable of increasing intracellular magnesium concentrations, whereas other magnesium supplements merely increase extra-cellular magnesium levels, which may result in less of a therapeutic effect or none at all. Two magnesium complexes that have been proposed to increase intracellular concentrations are magnesium orotate and magnesium aspartate.

Like many metal-containing complexes, the different magnesium compounds have different mechanisms of uptake in vivo. Additionally, upon administration, including ingestion, the transition metal complexes may undergo any number of reactions in vivo that affect the bioavailability and resulting therapeutic effect. By way of example, magnesium citrate is soluble in gastric fluid and thus is readily available for passive absorption in the upper gastrointestinal tract. Magnesium and taurine may act to improve insulin sensitivity and to reduce vasoconstriction and atherogenesis, and stabilize platelets. Magnesium acetate, magnesium ascorbate and magnesium lactate are soluble in gastric fluid and share the upper gastrointestinal passive absorption potential of magnesium citrate. The ascorbate radical serves as a source of vitamin C by conversion to ascorbic acid upon exposure to hydrochloric acid in the gastric fluid, whereas the magnesium ion is converted to soluble magnesium chloride. The satisfactory water solubility of magnesium acetate, magnesium ascorbate, magnesium citrate and magnesium lactate provide for a diffusional gradient of magnesium in the upper small intestine where some passive absorption of magnesium occurs. Magnesium oxide is converted to magnesium chloride in the stomach, and offers the advantage of a high ionic magnesium content, since 60% by weight of the magnesium oxide molecule is elemental magnesium. Magnesium diglycinate represents a form of magnesium that is absorbed in part as an intact dipeptide in the proximal small intestine via a dipeptide transport pathway and therefore provides a third absorptive mechanism for magnesium. Magnesium stearate is useful as a lubricant when compressing the composition into tablets. The observations for these magnesium complexes is illustrative of the type of processes and chemical reactions that may occur for any of the transitional metal complexes described herein, including the chromium- and vanadium-containing complexes.

A variety of dosages, in amount of magnesium, are contemplated by the present invention. Unless expressly provided otherwise, the dose amounts referred to herein refer to the amount of magnesium in any particular form, such as any particular complex. The dose may range from about 5 mg or less to 1000 mg or more. Specific dosages include about 5 mg, 10 mg, 20 mg, 40 mg, 50 mg, 80 mg, 100 mg, 150 mg, 250 mg, 500 mg, 750 mg, 1000 mg, 1500 mg, and 2000 mg. A preferred dose is 46 mg of magnesium. Typically, these are daily dosages. Higher dosages, while the may be daily dosages, may be used as short term regimes (e.g. less than about one month) and may tamper into dosages in the lower end of the ranges. In many such instances it will be advantageous to not to fall below about 40 to 100 mg per day of magnesium when tampering the dose. As for the chromium and vanadium components, the appropriate dose of magnesium may be based on the weight of the intended recipient. Alternatively, as discussed for other components, the appropriate dose of magnesium may be based on the condition of any subject, as assessed by a number of variables of import. Alternatively, the dosages may depend on the mode of administration. Alternatively, magnesium does may vary with the identity and amounts of the other components in any supplement of the present invention. As for the other components of the subject compositions, appropriate dosages may depend on numerous factors, and may be readily determined by one of skill in the art.

3.2.4 Aspirin (acetyl salicylic acid) and Other Anti-platelet Agents

Aspirin (e.g. acetyl salicylic acid) may be use to reduce the risk of either primary (high risk for cardiovascular disease) or secondary (cardiovascular disease). The health promoting benefits of aspirin derive in part from its anti-platelet effect. It appears to work, in part, by inhibiting cyclooxygenase, an enzyme necessary for the synthesis of thromboxane, a potent stimulator of platelet aggregation, a condition known to be increased in diabetes and to be causative in the atherosclerotic process. In patients with diabetes and other glucose metabolism disorders, aspirin appears to correct this abnormal increase in platelet activity.

Platelet aggregation is implicated in thrombus formation, which involves interaction of aggregated platelets and activated coagulation factors with a damaged vascular wall. Platelets are normally non-adherent, but upon damage to the endothelial lining of a vessel, the platelets adhere to exposed subendothelial collagen. The von Willebrand factor (vWF) is involved in this adhesion. Collagen and thrombin initiate platelet activation and activate phospholipase C, which hydrolyzes membrane phospholipids. Protein kinase C is thereby activated, and the calcium concentration of platelet cytosol increases. Arachidonic acid is liberated from membrane phospholipids and is oxidized in part to prostaglandin $H_2$ ($PGH_2$) and $TxA_2$. After platelet aggregation, fibrinogen is converted to fibrin to secure the hemostatic platelet plug. Platelet aggregation is mediated by the $PGH_2$ derivative prostacyclin, which is also a vasodilator. In the arachidonic acid cascade, aspirin acts as a cyclooxygenase inhibitor, blocking the conversion of arachidonic acid to the $PGH_2$ precursor prostaglandin $G_2$ ($PGG_2$). Because $PGG_2$ is a precursor to both $TxA_2$ and prostacyclin, aspirin blocks both the aggregation inducing and aggregation inhibiting effects of these factors.

Like aspirin, naproxen, indomethacin, piroxicam and acetaminophen inhibit production of the pain-producing prostaglandins by cox-2, but they all, other than aspirin, substantially inhibit cox-1, which produces prostacyclin. Aspirin inhibits prostacyclin production the least (3–4 hrs), and piroxicam the most (3–4 days). It is believed that that one aspirin taken every 3 days maximizes prostacyclin production and minimizes production of $TxA_2$, which causes hypertension and has been implicated in development of vascular disease. Other non-cyloooxygenase inhibitors may be used for pain relief in addition to aspirin (e.g., Tramadol-Ultram), or inhibitors of cox-2 only (e.g., Meloxicam, and Sulindac (Clinoril)).

Because aspirin in doses above 80 mg per day may interfere with the synthesis of prostaglandins necessary to protect the gastric mucosa, gastrointestinal hemorrhage may result if aspirin is used above such a dose. Therefore, aspirin trials have used progressively smaller doses to avoid the risk of hemorrhage, and have found comparable suppression of thromboxane with doses as low as 10 mg per day and with equal or greater risk reduction for cardiovascular end point.

In certain embodiments, the present invention may use standardized willow bark as the source of aspirin. Standardized willow bark is a Chinese herb and is highly standardized source of aspirin. Alternatively, other, naturally occurring sources of acetyl salicylic acid may be used in the present invention. Typical dosage ranges of acetyl salicylic acid include less than 10 mg to 100 mg or more. Particular doses of aspirin include about 5 mg, 10 mg, 20 mg, 40 mg, 50 mg, 60 mg, 80 mg, 100 mg, 150 mg, 200 mg. Typically, these are daily dosages. Generally, although higher dosages are contemplated by the invention, they are less preferred because of potential gastric disturbances. In certain embodiments, it will be advantageous not to fall below about 40 to 80 mg per day when tolerable by a patient. As for the other components of the subject compositions, the appropriate dose of aspirin may depend on the mode of administration. As for the other components of the subject compositions, appropriate dosages may depend on numerous factors, and may be readily determined by one of skill in the art. Such factors include the weight of the intended recipient or the condition of the recipient.

3.2.5 Folic Acid

It is now well recognized that elevated blood homocysteine (a sulfhydryl-containing amino acid) levels are a cardiovascular risk factor. Homocysteine may injure arterial endothelial cells, may affect platelet-endothelial cell interaction, and may be thrombogenic. Such effects appear to accelerate the artherogenic process in diabetic patients. High homocysteine levels may be normalized by folic acid treatment, which thereby may reduce artherscleotic events.

As with other the compounds of the present invention, the present invention may be practiced in the absence of folic acid, although in certain embodiments, the present invention will contain about 400 to about 600 mcg folic acid, or alternatively, about 400 mcg. Other possible doses include about 200 mcg or less, 300 mcg, 500 mcg, 600 mcg, 30 and about 1000 mcg or more.

3.2.6 Vitamin E and Other Anti-oxidants

There is evidence that diabetes produces oxidative stress that may be related to the many of the complications that accompany diabetes, including cardiovascular problems. Therefore, any compounds useful in reducing such stress may be valuable in the supplements of the present invention. Some possible candidates include the following:

a. Vitamin E

Vitamin E (free 2R,4'R,8'R-alpha-tocopherol) is the most widely studied of the antioxidant vitamins. The interest in vitamin E as an antioxidant is based on the many demonstrations in humans that giving vitamin E as a supplement decreases the oxidation of low density lipoprotein (LDL) ex vivo, an event critical in the atherogenic process.

It is believed that Vitamin E supplementation reduces significantly atherosclerosis in primates, including humans. This observation assumes greater importance in those with diabetes, in view of the fact that as many as 60% of newly diagnosed diabetic patients already have clinically obvious cardiovascular disease. A number of studies confirm such observation/A significantly lower risk of coronary artery disease was observed in a four year, prospective, observational study in healthy middle-aged men who had higher intakes of dietary vitamin E as compared to those consuming small amounts. In another prospective, epidemiological study, middle-aged women free of cardiovascular disease at baseline were found to have a highly significant reduced risk of coronary artery disease if they had been on vitamin E supplements for at least two years during the eight year study. In a more recent and similar seven year prospective study of postmenopausal women without cardiovascular disease, dietary vitamin E consumption, but not vitamin A or C, was inversely associated with the risk of death from coronary artery disease.

The Cambridge Heart Antioxidant Study ("CHAOS") investigated vitamin E supplementation in patients with coronary artery disease. CHAOS was a nearly three year prospective, secondary interventional trial of 2002 men and women, 10% of whom had diabetes, using vitamin E (free 2R,4'R,8'R-alpha-tocopherol), 400 or 800 I.U. daily, in a randomized, placebo-controlled, double-blinded design.

Either dose of vitamin E was associated with a dramatic and significant reduction of non-fatal myocardial infarction. The benefit of treatment with vitamin E was apparent after two hundred days, and the patients with diabetes also enjoyed the marked reduction in the risk of non-fatal heart disease.

Another benefit of vitamin E supplementation is believed to be the favorable effect it has on insulin sensitivity, glucose metabolism, and lipid levels in both healthy subjects and patients with Type 2 diabetes. Conversely, in a prospective study of almost one thousand non diabetic, middle-aged men, low concentration of plasma vitamin E at baseline was found to be an independent and powerful predictor for the development of Type 2 diabetes during the four year study. A low level of vitamin E was associated with a greater than five-fold risk of developing diabetes in the ensuing four years. In addition, vitamin E may restore reduced prostacyclin synthesis, thereby possibly treating neuropathy.

Vitamin E was well tolerated in the studies where it was given as a supplement, and in the CHAOS study, there was no difference between the alpha-tocopherol treatment (400 or 800 I.U.) or placebo groups for side effects. Because of the unusually high incidence of clinical heart disease in newly diagnosed diabetic patients, and the favorable effect vitamin E has on the metabolic abnormalities of Type 2 diabetes, the present invention may contain vitamin E. Dosages may range up to 1200 I.U. or more, especially 400–800 I.U., and particularly 400 I.U.

In addition to using alpha-tocopherol and its analogs and esters thereof, e.g., alpha-tocopherol acid succinate and alpha-tocopherol acetate, other equivalents of tocopherols may be used in the subject preparations, such as tocotrienols and their esters, and tocopheryl nicotinate. Gamma tocopherol are believed to trap mutagenic electrophiles such as NOx. Alpha-tocopherol acid succinate may be useful for preparing supplements in tablet form.

b. Alpha-lipoic Acid

Alpha-lipoic acid is a antioxidant and is an essential a coenzyme in the utilization of sugar (glucose) for energy production. Alpha-lipoic acid also assists the body recycle and renew other antioxidants, e.g. vitamins C and E, Co-Q1O and glutathione, and neutralizes both oxygen and nitrogen free radicals, which are believed to play major causal roles in cardiovascular diseases. It has been suggested that alpha-lipoic acid may increase intracellular glutathione levels. More recently, administration of alpha-lipoic acid to diabetic patients with neuropathy appeared to reduce significantly associated symptoms. In addition, DL-lipoic acid has been recommended for treatment of a metabolic aberration of pyruvate dehydrogenase, which is symptomatic of diabetes. Also, alpha-lipoic acid has been used to treat circulatory problems resulting from diabetes.

In certain embodiments, the present invention will contain about 10 mg or less to about 600 mg or more alpha-lipoic acid, with the most preferred dose of 50 mg. Other possible dosages include 10 mg or less, 25 mg, 75 mg, 100 mg, 150 mg, 200 mg, 250 mg, 300 mg, 400 mg, 500 mg, 600 mg, and 750 mg or more. If a patient presents with neuropathy, an increased dose of alpha-lipoic acid may be appropriate.

c. N-acetylcysteine

N-acetylcysteine (NAC) is a precursor to glutathione peroxidase. Evidence suggests that NAC has an affect on several conditions related to diabetes. For example, dietary NAC appeared to inhibit the development of peripheral neuropathy in STZ-induced diabetic rats. Sagara et al., *Diabetologia* 39:263–69 (1996). Administration of NAC was shown to reduce apolipoprotein A1 by over 20% in NIDDM patients. Gilligan et al., *Biochem. Biophys. Acta* 1254:187–92 (1995). Dosages may vary up to 1500 mg or more, and include dosages of 250 mg, 500 mg, 1000 mg, 1500 mg, and 2000 mg.

d. Selenium

Selenium may be present as atomic selenium, but may also be a selenium compound, organic or inorganic. Any selenium compound that is non-toxic at the levels administered, and capable of being formulated with the other compounds of the formulation may be used. Examples of inorganic sources of selenium may include sodium selenite, selenium chloride, selenium oxide, selenium sulfide, sodium selenide, sodium selenate, selenium bromide, selenium oxybromide, selenium fluoride, selenium oxyfluoride, selenium oxychloride, selenium hexafluoride, selenium tetrabromide, selenium tetrachloride and selenium tetrafluoride. Organic selenium is available, for example, as kelp bound selenium contained in a colloidal polymannuronate complex or as Selen-yeast which is yeast grown on media rich in selenium and/or selenium salts. Other useful organic sources include, for example, seleno-amino acids, seleno-proteins, selenium-rich extracts of biological materials, selenols such as methyl selenol and ethyl selenol, and selenophenols such as selenophenol itself. Dose may range up to 200 mcg or more (based on elemental selenium), and particular dosages include 40 mcg or less, 60 mcg, 80 mcg, 100 mcg, 150 mcg, 200 mcg, and 250 mcg or more.

Another possible component for improving anti-oxidant capabilities is ginko biloba extract. A possible dose is 120 mg, but the dose may vary. Finally, other well-known anti-oxidants that are contemplated by the present invention include both synthetic and naturally occurring ones: vitamin A ($\beta$-carotene and other carotenoids) vitamin C, selenium, probucol, drugs that inhibit superoxide anion formation or increase its destruction, and lipoxygenase inhibitors. In addition, diets rich in oleic acid may prove useful.

3.2.7 Vitamin A

The present invention contemplates formulations containing vitamin A, including retinoids, $\beta$-carotene, $\beta$-carotene, cryptoxanthine, and other equivalents. Possible dosages of Vitamin A or its equivalents include up to 5000 I.U. or more.

These components may be combined in certain embodiments with other vitamin and mineral supplements. These additional ingredients may be taken simultaneously. Other vitamins and minerals are important in the metabolism of glucose and the maintenance of good health and may be ingested from food or included in a supplement. Some of these other vitamins and minerals include calcium, copper, and zinc.

It should be recognized that the amounts of these vitamins and minerals may vary widely within the scope of the present invention.

3.3 Pharmacogenetics

In another aspect, embodiments of the present invention are directed to diagnostic and prognostic methods for determining whether a subject is at risk for developing diabetes, and in particular, Type 2 diabetes. Knowledge of a predisposition to developing impaired glucose metabolism allows for customization of a therapy or treatment regimen to an individual's genetic profile, which is aim of pharmacogenomics. The comparison of an individual's profile to the population profile for the disease permits the selection or design of supplements that are expected to be safe and efficacious for a particular patient or patient population (i.e., a group of patients having the same genetic alteration).

In particular, genetic screening would allow individuals that may be susceptible to diabetes to be identified readily, whereupon treatment with supplements of the present invention may be used to treat and/or prevent any disorders or conditions related to diabetes before onset of clinical symptoms. In addition, administration of a supplement of the present invention, with respect to both the effective dose and the timing of administration, may be optimized for different genetic populations.

Family studies point to a major genetic component in diabetes. Newman, et al., *Diabetologia* 30:763–68 (1987): K öbberling, *Diabetologia* 7:46–49(1971); Cook, *Diabetologia* 37:1231–40 (1994). The disease is believed to be polygenic in nature. Permutt et al., *Recent Progress in Hormone Research* 53:201–16 (1998).

A number of genotypes have been associated with different forms of diabetes. Mutations in human HNF genes may result in Type 2 diabetes. U.S. Pat. Nos. 5,795,726; 5,800,998. For instance, genetic lesions that may cause or contribute to diabetes include alterations affecting the integrity of a gene encoding an HNF1 and/or 4 protein, or the mis-expression of the HNF1 and/or 4 gene. A large number of assay techniques for detecting lesions in an HNF1 and/or 4 gene are described in the two above-referenced patents. Many of these assay techniques involve amplification of nucleic acids, often by polymerase chain reaction (PCR) or related techniques. Others use antibodies directed against wild type or mutant HNF1 and/or 4 proteins. The assay methods described therein may be performed, for example, by utilizing pre-packaged diagnostic kits comprising at least one probe nucleic acid or antibody reagent described therein, which may be conveniently used, e.g., in clinical settings to diagnose patients exhibiting symptoms or family history of a disease or illness involving an HNF1 and/or 4 gene.

In another report, genetic mutations in mitochondrial genes were observed to segregate with late onset diabetes. U.S. Pat. No. 5,840,493. Mutations in two genes, mitochondrial ATP synthase gene and mitochondrial tRNA lysine gene, were reported to correlate with the presence or risk of Type 2 diabetes. In another report, a non-conservative missense mutation in the β-3-adrenergic receptor is associated with susceptibility to, and development of Type 2 diabetes and obesity. U.S. Pat. No. 5,766,851. The responsible mutation is at codon 64. The present invention contemplates screening for mutations or genetic lesions in these genes to identify individuals that might benefit from administration of the subject supplements before the on-set of Type 2 diabetes and thereafter.

In addition, the genetic basis of a few rare monogenic syndromes of Type 2 diabetes have been elucidated. Linkage to diabetes was observed to rare early-onset forms of Type 2 diabetes that is associated with chronic hyperglycemia and monogenic inheritance (MODY loci). Bell et al., *Proc. Natl. Acad. Sci. USA* 88:1484–88 (1991); Froguel et al., *Nature* 356:162–64 (1992); Hattersley et al. *Lancet* 339:1307–10 (1992); Vaxillaire et al., *Nature Genet.* 9:418–23 (1995). The defects in the glucokinase (GCK) gene on human chromosome 7 have been found to be responsible for the relatively rare MODY2 phenotype. Froguel et al., supra.

The genes responsible for MODY1 and MODY3 have not as yet been identified. However, linkage studies have shown that MODY1 is tightly linked to the adenosine deaminase gene (ADA) on human chromosome 20q. Bell et al., supra; Cox et al., *Diabetes* 41:401–07 (1992); Bowden et al., *Diabetes* 41:88–92 (1992). In addition, the MODY1 locus has been refined to a 13 centimorgan interval (about 7 Mb) on chromosome 20 in bands q11.2–q13.1. Rothschild et al., *Genomics* 13:560–64 (1992). Linkage studies have shown that the gene responsible for MODY3 is contained within a 7 centimorgan interval bracketed by D12586 and D125342 on human chromosome 12q. Vaxillaire et al., *Nature Genetics* 9:418–23. (1995). The MODY3 gene was not found to be implicated in late-onset Type 2 diabetes. Lesage et al., *Diabetes* 44:1243–47 (1995).

Another locus has been identified for a rare early-onset form with mitochondrial inheritance. Van den Ouwenland et al., *Nature Genet.* 1:368–71 (1992). In addition, Harris et al. identified a locus of NIDDM1 on chromosome 2 that appears to play a role in Mexican American diabetes. Harris et al., *Nature Genet.* 13:161–66 (1996). Further, Mahtani et al. report evidence of the existence of a gene on human chromosome 12, NIDDM2, that causes Type 2 diabetes associated with low insulin secretion. Mahtani, et al., *Nature Genetics* 14:90–94 (1996). Mahtani et al. suggest that NIDDM2 and MODY3 represent different alleles of the same gene with severe mutations causing MODY3 and milder mutations giving rise to later-onset Type 2 diabetes characterized by low insulin secretion.

Other reports indicate that diabetes-causing genes may be specific to individual ethnic groups. As a result, the present invention contemplates preparing kits containing the proper materials and supplies for the appropriate genetic testing of discrete subpopulations, along with, in certain embodiments, the treatment and prevention regimens disclosed herein. For example, in the Oji-Cree people of Northern Ontario, who have the world's third highest prevalence of Type 2 diabetes, diabetic adults have a high frequency of a mutation, G319S, which affects the structure of HNF-1α.

As additional genetic lesions that may cause or contribute to diabetes are reported or discovered, the present invention contemplates using them as diagnostic or prognostic indicators for susceptibility to diabetes, especially Type 2 diabetes. The supplements of the present invention may be used preventively to ameliorate conditions in individuals displaying a genetic profile with an increased risk for diabetes.

In yet another means of screening for diabetes, the levels of expression at the mRNA of human insulin receptors A and B (HIR-A and HIR-B, respectively), have been associated with Type 2 diabetes or a genetic predisposition to Type 2 diabetes. U.S. Pat. No. 5,719,022. A ratio of 1:1: in the two mRNA levels is indicative of Type 2 diabetes or a susceptibility to Type 2 diabetes.

3.4 Dosage and Assays of Supplements, or Components Thereof

The dosage of any anti-diabetic agent or supplement, or any component thereof, of the present invention will vary depending on the symptoms, age and body weight of the patient, the nature and severity of the disorder to be treated or prevented, the route of administration, and the form of the supplement. Possible dosage ranges and particular dosages have been presented above in discussing different components that may be present in any supplement or composition of the present invention. Any of the subject formulations or anti-diabetic agents may be administered in a single dose or in divided doses. Dosages for many of the anti-diabetic agents discussed herein are known in the art. Dosages for anti-diabetic agents or supplements, or components thereof, may be readily determined by techniques known to those of skill in the art or as taught herein.

An effective dose or amount, and any possible affects on the timing of administration of the formulation, may need to be identified for any particular anti-diabetic agent or supplement, or component thereof, of the present invention. This may be accomplished by routine experiment as described herein, using one or more groups of animals (preferably at least 5 animals per group), or in human trials if appropriate. The effectiveness of any supplement and method of treatment or prevention may be assessed by administering the supplement and assessing the effect of the administration by measuring one or more indices associated with glucose metabolism, and comparing the post-treatment values of these indices to the values of the same indices prior to treatment.

The precise time of administration and/or amount of any particular anti-diabetic agent or supplement that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, glucose metabolism may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of three months being a typical length of therapy for humans.

Adjustments to the amount(s) of agent(s), drug(s), or supplement(s) administered and possibly to the time of administration may be made based on these reevaluations. For example, if after four weeks of treatment one of the metabolic indices has not improved but at least one other has, the dose of different components of the formulation might be increased by, for example, one-third. For example, if blood glucose levels have not decreased sufficiently after a period of treatment by a formulation of the present invention, then the dosages of chromium and vanadium-containing complexes may be increased, or alternatively other complexes may be used, whereas the dose of aspirin would not necessarily need to be adjusted.

Treatment may be initiated with smaller dosages which are less than the optimum dose of the compound. Thereafter, the dosage may be increased by small increments until the optimum therapeutic effect is attained.

The combined use of several components in any supplement in conjunction with an anti-diabetic agent of the present invention may reduce the required dosage for any individual component because the onset and duration of effect of the different components may be complimentary. In such combined therapy, the different components and/or anti-diabetic agent(s) may be delivered together or separately, and simultaneously or at different times within the day. Often, the different components or antidiabetic agent(s) may be administered substantially simultaneously, or alternatively as a composition or formulation containing both components. For example, it is known that vitamin C may regenerate and spare vitamin E, so any formulation having both of these compounds may provide complimentary protection against oxidative stress.

For assaying different anti-diabetic agents, supplements, or components thereof, and different treatment regimens, a variety of indices may need to be measured. For example, in an oral glucose tolerance test, a patient's physiological response to a glucose load or challenge is evaluated. After ingesting the glucose, the patient's physiological response to the glucose challenge is evaluated. Generally, this is accomplished by determining the patient's blood glucose levels (the concentration of glucose in the patient's plasma, serum, or whole blood) at several predetermined points in time. Guyton, *Textbook of Medical Physiology* 855–67 ($8^{th}$ ed. 1991). Another related method is the hyperinsulinemic-euglycemic clamp.

Blood glucose measurements may be made by any number of methods. The timing of any blood glucose test may be material, and the present invention contemplates determining the fasting blood glucose level and especially the post-prandial blood glucose level. In general, the desirable fasting glucose level (or pre-prandial) is 80 to 120 mg/dL, and a non-diabetic has a pre-prandial glucose level of less than 110 mg/dl. The desirable post-prandial level (or bedtime glucose level) is 100 to 140 mg/dL, and a non-diabetic has a bedtime glucose level of less than 120 mg/dl. Under the American Diabetes Clinical Practice Recommendations, additional action is recommended if the fasting blood glucose level is greater than 140 mg/dl or the post-prandial glucose level is greater than 160 mg/dl. For older patients, or those with related complications, different treatment goals may be appropriate.

Some measurement methods for glucose employ invasive techniques, which require taking a blood sample from the subject. Many invasive glucose sensors are based on electrochemical methods such as the electroenzymatic method. Three enzymes are often used: glucose oxidase, hexokinase and glucose dehydrogenase. For example, blood glucose is oxidized by glucose-oxidase to produce gluconic acid and hydrogen peroxide. Glucose concentrations may be determined by measuring oxygen consumed or hydrogen peroxide produced (amperometric method), or by measuring gluconic acid produced (potentiometric method).

Alternatively, it may be possible to determine blood glucose levels by using non-invasive methods. Non-invasive technologies that have been used or proposed for measuring glucose levels in tissue include: near-IR transmission and reflectance, Near-IR Kromoscopy, spatially resolved diffuse reflectance, polarimetry measurements, raman measurements, and PA measurements. In another example, it is possible to monitor a patient's blood glucose levels and insulin levels by monitoring ECG changes upon glucose uptake. This method does not work for Type 1 diabetic patients, however, because they lack the necessary pancreatic insulin response. In another method, blood glucose levels may be measured by irradiating blood vessels in the retina of the eye. Finally, other spectroscopic methods have been proposed and are known to those of skill in the art.

Another clinical index for glucose metabolism is glycosylated hemoglobin A. Human adult hemoglobin (Hb) typically consists of HbA, HbA2, and HbF. These forms of hemoglobin differ by virtue of their primary structure (i.e., amino acid sequence). Normally, HbA constitutes about 97% of the total hemoglobin present, HbA2 constitutes about 2.5% of the total, and HbF, also known as fetal hemoglobin, only about 0.5%.

Chromatographic analysis of HbA has shown that it contains a number of minor hemoglobin species. These minor species have been designated HbA1a, HbA1b, and HbA1c. These species are referred to as glycosylated hemoglobins or glycohemoglobins, and are formed by condensation of the amino group of the hemoglobin with a keto moiety of a sugar. For HbA1c, the sugar is glucose, and the glycosylated hemoglobin is formed by the condensation of the N-terminal valine amino acid of each β-chain of hemoglobin with glucose to form an unstable Schiff base or aldimine (also known as pre-A1c), which then undergoes an Amadori rearrangement to form a stable ketoamine. Methods have been developed to distinguish between the stable and labile forms of HbA1c so as to provide more accurate measurements of the stable HbA1c.

The formation of glycosylated hemoglobins is non-enzymatic and occurs over the lifespan of the red cell, which is about 120 days under normal conditions. The amount of HbA1c is proportional to the concentration of glucose in the blood, and is therefore related to time-averaged glucose concentration over the period prior to the measurement, which is approximately two to three months. HbA1c values may be used to assess diabetic control, in which short-term fluctuations in plasma glucose levels do not affect the measurement. In general, the desirable HbA1c level is less than 7%, and less than 6% in a non-diabetic. Under the American Diabetes Clinical Practice Recommendations, additional action is recommended if a patient's HbA1c level exceeds 8%. VHA guidelines recommend measuring HbA1c levels at least once annually.

Measurement of glycosylated hemoglobins may augment other traditional methods of assessing control of glucose metabolism. For example, measurement of glycosylated hemoglobins may be used when urine glucose records are inadequate, when blood glucose levels vary markedly throughout the day or from day to day, and for a new patient with known or suspected diabetes in whom there is no previous record of blood glucose concentration. A particular application for monitoring glycosylated hemoglobins is during pregnancy, when close control of diabetes is especially important.

There are a number of currently available methods for determining levels of glycosylated hemoglobins, including ion exchange chromatography, high-performance liquid chromatography, affinity chromatography, colorimetry, radioimmunoassay, electrophoresis, and isoelectric focusing. Ion exchange chromatography may be conducted using resins containing weakly acidic cation exchanges or negatively charged carboxymethylcellulose resin. High performance liquid chromatography provides a reliable reference method.

Affinity chromatography may be used to separate non-glycosylated hemoglobin from glycosylated hemoglobin. A suitable affinity column is prepared having immobilized m-aminophenylboronic acid. The boronic acid reacts with the cis-diol groups of glucose bound to hemoglobin to form a reversible 5-membered ring complex, thus selectively binding the glycosylated hemoglobin to the affinity column. Sorbitol disassociates glycosylated hemoglobin from the column. For example, glycosylated hemoglobin may be measured by a modification of the method of Clegg and Schroeder, Clegg et al., *J. Lab Clin. Med.* 102:577–89 (1983).

A calorimetric method has been devised based on the observation that HbA1c, when subject to mild acid hydrolysis, releases 5-hydroxymethylfurfural (5-HMF). Another spectrophotometric method involves the reaction of inositol hexaphosphate (phytic acid) with hemoglobin. Absorbance increases at 633 nm and decreases at 560 nm. upon phytic acid binding to the N-terminal amino groups of the β-chains. This change only occurs for Hb A that is unglycosylated, so the change in absorbance induced by phytic acid is thus inversely proportional to the fraction of glycosylated hemoglobin.

Antibody directed against HbA1c may be prepared and used as the basis for a radioimmunoassay. Isoelectric focusing has also been used as a method of quantitating HbA1c. In another method capillary electrophoresis may be used, usually in conjunction with an antibody directed against HbA1c.

Kits for measuring glycosylated hemoglobin are known in the art, and contemplated by the present invention.

Fasting glucose levels may be measured by finger stick glucometer readings. Samples of apolipoproteins may be analyzed on a protein analyzer using proper standardization techniques. Other indices may be measured by techniques known to those of skill in the art.

Animal-based studies may be conducted on different anti-diabetic agents, supplements, or components thereof, of the present invention as necessary to determine combinations of the different components that produce the greatest therapeutic effect. For example, in rats the diabetic state may be induced by injecting streptozoticin (STZ) at an appropriate dose, for example 60 mg/kg dissolved in 0.9% NaCl IC via the tail vein upon anaesthetization. The diabetic state may be confirmed at a later time, whereupon assaying of different supplements may begin thereafter. Alternatively, insulin resistant spontaneously hypertensive rats (SHR) made be used, with the genetic control being the Wistar Kyoto (WKY) strain. Alternatively, the Zucker diabetic fatty rat (ZDF) a model of spontaneous NIDDM, may be used, with the Zucker lean control (ZLC) rats as controls. In addition, transgenic mouse models may be useful in the present invention.

Alternatively, the db/db mouse, a genetically obese and diabetic strain of mouse, may be used in animal studies. The db/db mouse develops hyperglycemia and hyperinsulinemia concomitant with its development of obesity and thus serves as a model of obese Type 2 diabetes. The db/db mice may purchased from, for example, the Jackson Laboratories (Bar Harbor, Me.). In an exemplary embodiment, for treatment of mice with a regimen including a formulation of the present invention or control, sub-orbital sinus blood samples may be taken before and at some time after dosing of each animal.

Toxicity and therapeutic efficacy of anti-diabetic agents, supplements, or components thereof, may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio $LD_{50}/ED_{50}$. Compositions that exhibit large therapeutic indices are preferred. Although supplements that exhibit toxic side effects may be used, care should be taken to design a delivery system that targets the component(s) of any supplement responsible for any toxic effects to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For any supplement or components thereof of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

3.5 Formulations of Supplements, or Components Thereof

The anti-diabetic agents, compositions and supplements of the present invention may be administered in various forms, depending on the disorder or condition to be treated and the age, condition and body weight of the patient, as is well known in the art. It will also be appreciated that each of the different components can be administered individually, or alternatively each can be formulated into one medicament for administration to the patient. In preferred embodiments, each of the different components is formulated as a tablet, capsule, or other appropriate ingestible formulation as discussed in more detail below, to provide a therapeutic dose in ten tablets or fewer. In particularly preferred embodiments, a therapeutic dose is provided in five tablets or fewer. In most preferred embodiments, a therapeutic dose is provided in three tablets or fewer. For any of the modalities presented herein, different anti-diabetic agents or components of any subject supplement may be administered by different methods as necessary for effective delivery of the component, or as otherwise necessary for convenience. For example, where the formulation is to be administered orally, it may be formulated as tablets, capsules, granules, powders or syrups. Alternatively, formulations of the present invention may be administered parenterally as injections (intravenous, intramuscular or subcutaneous), drop infusion preparations, or suppositories. For application by the ophthalmic mucous membrane route, they may be formulated as eyedrops or eye ointments. These formulations may be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent.

In formulations of the subject anti-diabetic agents, supplements and compositions, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the supplements.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of supplement or components thereof which may be combined with a carrier material to produce a single dosage form will vary depending upon the subject being treated, and the particular mode of administration. The amount of active ingredient which may be combined with a carrier material to produce a single dosage form will generally be that amount of the compound which produces a therapeutic effect. Generally, out of one hundred percent, this amount may range from about 1 percent to about ninety-nine percent of active ingredient, particularly from about 5 percent to about 70 percent, especially from about 10 percent to about 30 percent.

Methods of preparing these formulations or compositions include the step of bringing into association a supplement or components thereof with the carrier and, optionally, one or more accessory ingredients. In general, the formulations are prepared by uniformly and intimately bringing into association a supplement or components thereof with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a supplement or components thereof as an active ingredient. A supplement or components thereof may also be administered as a bolus, electuary, or paste.

In solid dosage forms for oral administration (capsules, tablets, pills, dragees, powders, granules and the like), the supplement or components thereof is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the supplement or components thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Tablets and other solid dosage forms may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which may be dissolved in sterile water, or sonic other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient may also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the supplement or component, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, coloring, perfuming and preservative agents.

Suspensions, in addition to the supplement or components thereof, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more component with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for transdermal administration of an anti-diabetic agent, supplement or component includes powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required. For transdermal administration of transition metal complexes, the complexes may include lipophilic and hydrophilic groups to achieve the desired water solubility and transport properties.

The ointments, pastes, creams and gels may contain, in addition to a supplement or components thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a supplement or components thereof, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Anti-diabetic agent(s) or components of the supplement may alternatively be administered by aerosol. For example, insulin deliver by aerosol has been proposed, U.S. Pat. No. 5,813,397. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which may result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a component of a supplement to the body. Such dosage forms may be made by dissolving or dispersing the agent in the proper medium. Absorption enhancers may also be used to increase the flux of the component across the skin. The rate of such flux may be controlled by either providing a rate controlling membrane or dispersing the component in a polymer matrix or gel.

Ophthalmic formulations, eye ointments, powders, solutions and the like, are also contemplated as being within the scope of this invention.

Pharmaceutical compositions of this invention suitable for parenteral administration comprise one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These formulations may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of an anti-diabetic agent or component of a supplement, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of components of a supplement in biodegradable polymers such as polylactide-polyglycolide. Depending on the ratio of component to polymer, and the nature of the particular polymer employed, the rate of component release may be controlled. Examples of other biodegradable polymers include poly(orthoesters) and poly(anhydrides). Depot injectable formulations are also prepared by entrapping the component in liposomes or microemulsions which are compatible with body tissue.

EXEMPLIFICATIONS

The present invention now being generally described may be more readily understood by reference to the following examples which are included merely for purposes of illustration of certain aspects and embodiments of the present invention, and are not intended to limit the invention.

Example One

A supplement (detailed below) was administered daily to a female with Type 2 diabetes who was experiencing poor blood sugar control while taking metformin 500 mg b.i.d. In conjunction with continued metformin administration, the patient was given an oral daily nutritional supplement comprising the following ingredients: chromium 333 mcg (in the form of chromium picolinate/polynicotinate); magnesium 46 mg (in the form of 384 mg magnesium chloride); vanadyl-sulfate hydrate 100 mg; vitamin E 400 I.U, and folate 400 mcg.

The results are summarized below in Table 1

TABLE 1

| Therapeutic Regimen | HbA1c Level | Estimated Blood Sugar (mg/dL) | Fasting Blood Sugar (mg/dL) |
| --- | --- | --- | --- |
| Metformin alone | 9.7 | 200 | 185 |
| Metformin & composition (after 2 months) | 7.9 | 141 | 153 |

The above results indicate the degree to which a composition consisting of components and an anti-diabetic agent according to the present invention, administered in accordance with invention methods, may dramatically improve blood sugar control and reduce HbA1c levels when compared to treatment with an anti-diabetic agent alone, such as metformin.

In addition to the lowered HbA1c and fasting blood sugar levels, the patient experienced a significant lowering of total cholesterol and a concomitant lowering of triglyceride, HDL and LDL levels, as summarized below in Table 2.

TABLE 2

| Therapeutic | Cholesterol | LDL | HDL | Triglycerides |
| --- | --- | --- | --- | --- |
| Metformin alone | 229 | 133 | 52 | 220 |
| Metformin & composition (after 2 months) | 192 | 114 | 38 | 200 |

The results summarized in Table 2 indicate that a composition comprising components and an anti-diabetic agent according to the present invention, administered in accordance with invention methods, also dramatically reduces overall cholesterol levels, improves the LDL:HDL ratio and lowers serum triglyceride levels when compared to treatment with metformin alone.

Example Two

To further test the efficacy of inventive compositions, a certain embodiment of the present invention, the supplement detailed below, was administered daily to a 27 year old female with Type 2 diabetes who was experiencing poor blood sugar control while taking metformin 1000 mg b.i.d.

After 3 months of augmenting the daily regimen of 2000 mg metformin with the above oral nutritional supplement, the patient's HbA1c level dropped from 8.3 to 6.1. These results again serve to demonstrate the degree to which invention compositions, administered in accordance with invention methods, serves to beneficially lower a diabetic patient's HbA1c levels, even though the patient had experienced poor blood glucose control on high doses of metformin alone.

Example Three

In another example, a group of Type 2 diabetic individuals presenting with elevated HbA1c levels were placed on a program using a variety of embodiments of the present invention. The study was conducted as an open-label study at five different medical centers in the United States. The patients were on the program for three months, and were directed not to change their dietary habits or lifestyle, including exercise patterns.

For this Example Three, one daily dose of every embodiment contained, in addition to any of the anti-diabetic agents set forth in the accompanying tables, the following (component and amount):

Vitamin A, 5000 IU; Vitamin C (Ascorbic Acid), 60 mg; Vitamin D-3, 400 IU; Vitamin E (free 2R,4'R,8'R-alpha-tocopherol), 400 IU; Thiamine (as Thiamine Mononitrate), 3 mg; Riboflavin, 3.6 mg; Niacinamide, 20.1 mg; Vitamin B-6 (as Pyridoxine HCl), 23.1 mg; Folic Acid, 400 mcg; Vitamin B-12, 48 mcg; Biotin, 300 mcg; Pantothenic Acid (as Calcium Pantothenate), 10 mg; Calcium (from Calcium Carbonate/Phosphate), 150 mg; Phosphorous (from Calcium Phosphate), 115 mg; Iodine (from Sea Kelp), 150 mg; Magnesium (elemental Magnesium from 307 mg Magnesium Complex of citrate/fumarate/malate/gluturate-/succinate/chloride), 46 mg; Zinc, 15 mg; Selenium (from Selenium Krebs), 60 mcg; Manganese (from Manganese Sulfate), 11 mg; Chromium (from 3264 mcg Chromium Picolinate/Polynicotinate Complex (50%/50%)), 333 mcg; Vanadyl Sulfate hydrate, 100 mg; Willow (bark) (standardized willow/willow bark complex) (aspirin 20 mg), 160 mg. In the examples described herein, chromium picolinate was obtained from Nutrition 21 or AMBI Inc., and chromium polynicotinate was obtained from InterHealth. The vanadium sulfate hydrate in this example was determined to contain about 20% elemental vanadium by weight, which corresponds to about five to six waters of hydration for every molecule of vanadyl sulfate.

REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Patents and Patent Applications

U.S. Pat. No. Re. 33,988
U.S. Pat. No. 4,255,385

U.S. Pat. No. 4,959,222
U.S. Pat. No. 4,966,588
U.S. Pat. No. 5,045,316
U.S. Pat. No. 5,087,624
U.S. Pat. No. 5,212,154
U.S. Pat. No. 5,292,663
U.S. Pat. No. 5,431,793
U.S. Pat. No. 5,532,269
U.S. Pat. No. 5,599,835
U.S. Pat. No. 5,665,385
U.S. Pat. No. 5,710,630
U.S. Pat. No. 5,741,211
U.S. Pat. No. 5,789,401
U.S. Pat. No. 5,820,557
U.S. Pat. No. 5,824,840
U.S. Pat. No. 5,882,685
U.S. Pat. No. 5,866,619

Publications and Other References

Abbott et al, *JAMA* 260:3456–60 (1988)
Anderson, *J. Am. College Nutrition* 17:548–55 (1998).
American Diabetes Association, *Diabetes Care* 20 (Suppl. 1):S14–17 (1997)
Arsenian et al., *Prog. Cardiovasc.Dis.* 35:271–310 (1993)
Baker et al., *Diabetes Educ.* 18:420–27 (1992)
Barnard et al., *Diabetes Care* 17:1469–72 (1994)
Biernan et al., *Arterioscler. Thromb.* 12:647–56 (1992)
Bisse et al., *J. Chromatography* 434 95–110 (1988)
Busse et al., *Drug Res.* 42:829–31 (1992).
Caballero, *Nutr. Rev.* 51:339–340 (1993)
Cam et al., *Diabetologia* 36:218–24 (1993)
Chowdhury et al., *Postgrad Med. J.* 74:480–81 (1998)
Christen et al., *PNAS USA* 94:3217–22 (1997).
Clarke et al., *N. Eng. J. Med.* 325:1137–41 (1991)
Classen et al., 6 *Recent Advances in Studies on Cardiac Structure and Metabolism* 111–18 (University Park Press 1975)
Classen et al., *Magnesium* 3:257–64 (1984)
Clegg et al., *J. Lab Clin. Med.* 102:577–89 (1983)
Cohen et al., *JAMA* 249:2808–10 (1983)
Colwell et al., *Metabolism* 26:279–85 (1977)
Dai et al., *Pharmacol. & Toxicol.* 74:101–09 (1994)
Davi et al., *Arterioscler. Thromb.* 13:1346–49 (1993)
Davis et al., *Curr. Ther. Res.* 36:341–46 (1984)
Defronzo et al., *Diabetes Care* 14:173–94 (1991)
Dieber-Rotheneder et al., *J. Lipid Res.* 32:1325–32 (1991)
Drvota et al., *Adv. Prost. Throm. Leuk. Res.* 21A:153–56 (1990)
Entmacher et al., *Diabetes* 13:373–77 (1964)
Ewald et al., *Acta Paediatr. Scand.* 72:367–71 (1983)
Franz et al., *Diabetes Care* 17:490–518 (1994)
Freund et al., *JAMA* 241:496–98 (1979)
Goldstein, et al., *C.R.C. Critical Reviews in Clinical Laboratory Sciences* 21:187–228
Goyder et al., *BMJ* 317:1644–46 (1998)
Granberry et al., *Southern Medical J.* 92:2–14 (1999)
Guthrie et al., *Diabetes Care* 15:1494–98
Guyton, *Textbook of Medical Physiology* 855–67 (8th ed. 1991)
Haffner et al., *Diabetes* 41:715–722 (1992);
Hafffner et al., *JAMA* 263:1893–98 (1990);
Harris, in *Diabetes in America* (2d ed., NIH 1995)
Harris et al., *Diabetes Care* 15:815–19 (1992)
Heath et al., *Diabetologia* 7:308–15 (1971)
*International Textbook of Diabetes Mellitus* (Alberti et al. eds, John Wiley: 1992)

Jarrett et al., *Diabetologia* 22:79–84 (1982)
Javitt et al., in *Diabetes in America* (2d ed., NIH 1995)
Jeejeebhoy et al., *Am. J. Clin. Nutr.* 30:531–38 (1977)
Julkunen-Tiito et a;., *Planta Medica* 55:55 (1989)
Kalgutkar et al., *Science* 280:1268–70 (1998)
Kannel, *Am. Heart J.* 110:1100–07 (1985)
Kaplan, *Arch. Intern. Med.* 149:1514–20 (1989)
Khalil, *Clinical Chemistry* 45:165–77 (1999)
Klein et al., *Ophthalmology* 91:1–9 (1984)
Kruse-Jarres et al., *Clin. Chem. Clin. Biochem.* 26:201–08 (1988)
Kunisaki et al., *Metabolism* 41:613–21 (1992)
Kushi et al., *N. Engl. J. Med.* 334:1156–62 (1996)
Kuusisto et al. *Diabetes* 43:960–67 (1994)
Kwaan et al., *J. Lab. Clin. Med.* 20:235–46 (1972)
*Lancet* 336:827–30 (1990)
*Lancet* 338:1345–49 (1991).
Lardinois, *Geriatrics* 53:22–39 (1998)
Levine et al., *Diabetologia* 21:131–34 (1981)
Lee et al., *Ann. Intern. Med.* 120:184–90 (1994)
Lipid Research Clinic's Program, *JAMA* 251:351–74 (1984)
Lippard et al., *Principles of Bioinorganic Chemistry* (1994)
Malabu et al., *Diabetes* 43:9–15 (1994)
Margolis et al., *Am. J. Cardiol,* 31:1–7 (1973)
Marier, *Can. Biol.* 37:115–25 (1978)
Mertz, *Nutr. Rev.* 33:129–35 (1975)
McNair et al., *Eur. J. Clin. Invest.* 12:81–85 (1982)
McPhillips et al., *Am. J. Epidemiology* 131:443–53 (1990)
Molten et al., *Electrophoresis* 15:22–30 (1994)
Mooradian et al., *Diabetes Care* 17:464–79 (1994).
Orchard et al., *Circulation* 88:819–28 (1993)
Paolisso et al., *Am. J. Hypertens.* 10:346–55 (1997)
Paolisso et al., *Am. J. Clin. Nutr.* 57:650–56 (1993)
Paolisso et al., *Diabetes Care* 16:1433–37 (1993)
Preuss et al., *Clinical Nephology,* 47:325–30 (1997)
Reaven, *Diabetes* 37:1595–607 (1988)
Reinhart, *Arch Intern. Med.* 148:2415–20 (1988)
Resnick et al., *Am. J. Med.* 93 (Suppl. 2A):2A11S–2A20S (1992)
Rimm et al., *N. Engl. J Med.* 328:1450–56 (1993)
Rubin et al., *J. Clin. Endocrinol. Metab.* 78:809A–09F (1994)
Rude, *Am. J. Cardiol.* 63:31G–34G (1989)
Ryzen *Am. Heart J.* 111:475–80 (1986).
Saad et al., *Lancet* 1:1356–59 (1989)
Sagel et al., *Ann. Intern. Med.* 83:733–38 (1975)
Sakuri et al., *Biochem. Biophys Res. Commun.* 96:293–98 (1980)
Salonen et al., *BMJ* 311:1124–27 (1995)
Seelig et al., *Am. J. Cardio.* 63:4G–21G (1989)
Sjogren et al., *Acta Med. Scand.* 224:461–65 (1988)
Stamler et al., *Diabetes Care* 16:434–44 (1993)
Stampfer et al., *N. Engl. J. Med.* 328:1444–49 (1993)
Steinberg et al., *N. Engl. J. Med.* 320:915–20 (1989)
Steinberg, *Circulation* 85:2337–44 (1992)
Stephens et al., *Lancet* 347:781–86 (1996)
Tomlinson, *Diabetes & Metabolism (Paris)* 24:79–83 (1998)
Tosiello et al., *Arch Intern. Med.* 156:1143–48 (1996)
Tsui et al., *Endocrinologist* 5:263–71 (1995)
*USRDS 1994 Annual Data Report* (NIH 1994)
Vane, *Nature* 231:232 (1971)
Verlangieri et al., *J. Am. Coll. Nutr.* 11:131–38 (1992)
*Vital and Health Statistics* Series 10, no. 190 (1994)
Whang et al., *Am. J. Med.* 82 (Suppl. 3A):24–29 (1987)
Zeigler et al., *Diabetes Care* 20:369–73 (1997)

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising synergistic effective amounts of an anti-diabetic agent other than insulin, a bioavailable source of chromium, and a bioavailable source of vanadium, wherein said anti-diabetic agent is a sulfonylurea, and wherein components of said composition synergistically reduce the HbA1c levels of a patient by at least about 10% after treatment for a period of at least about thirty days with said composition as compared to treatment with said anti-diabetic agent alone.

2. The composition according to claim 1, wherein said sulfonylurea is one of the following: acetohexamide, chlorpropamide, tolazimide, tolbutamide, glycazide, glipizide, glyburide, or glimeperide.

3. The composition of claim 1, wherein said reduction in said Hb1Ac level is at least about 50%.

4. The composition of claim 1, wherein said bioavailable source of chromium comprises one or more of chromium picolinate or chromium polynicotinate.

5. A composition according to claim 4, wherein the bioavailable source of chromium is chromium picolinate and wherein the amount of chromium picolinate is from about 30 μg up to about 1000 μg, per dose.

6. A composition according to claim 4, wherein the bioavailable source of chromium is chromium polynicotinate and wherein the amount of chromium polynicotinate is from about 30 μg up to about 5000 μg, per dose.

7. The composition of claim 1, wherein said bioavailable source of chromium comprises no less than about 200 micrograms of elemental chromium.

8. The composition of claim 1, wherein said bioavailable source of chromium comprises no less than about 100 micrograms of elemental chromium.

9. The composition of claim 1, wherein said bioavailable source of chromium comprises no less than about 5 micrograms of elemental chromium.

10. The composition of claim 1, wherein said bioavailable source of vanadium is vanadyl sulfate.

11. The composition of claim 10, wherein the amount of vanadyl sulfate is in the range of about 20 mg up to about 100 mg, per dose.

12. The composition of claim 1, wherein said bioavailable source of vanadium comprises more than about 10 mg elemental vanadium.

13. The composition of claim 1, wherein said amount of said bioavailable source of vanadium comprises no less than 5 mg of elemental vanadium.

14. The composition according to claim 1, wherein said sulfonylurea is one of the following: acetohexamide, chlorpropamide, tolazimide, or tolbutamide.

15. The composition according to claim 1, wherein said sulfonylurea is one of the following: glycazide, glipizide, glyburide, or glimeperide.

16. The composition according to claim 1, wherein said sulfonylurea is glyburide.

17. The composition according to claim 1, wherein said sulfonylurea is glipizide.

18. The composition according to claim 1, wherein said sulfonylurea is glimeperide.

19. The composition according to claim 4, wherein said sulfonylurea is one of the following: acetohexamide, chlorpropamide, tolazimide, tolbutamide, glycazide, glipizide, glyburide, or glimeperide.

20. The composition according to claim 10, wherein said sulfonylurea is one of the following: acetohexamide, chlorpropamide, tolazimide, tolbutamide, glycazide, glipizide, glyburide, or glimeperide.

21. The composition according to claim 4, wherein said sulfonylurea is one of the following: acetohexamide, chlorpropamide, tolazimide, or tolbutamide.

22. The composition according to claim 4, wherein said sulfonylurea is one of the following: glycazide, glipizide, glyburide, or glimeperide.

23. The composition according to claim 10, wherein said sulfonylurea is one of the following: acetohexamide, chlorpropamide, tolazimide, or tolbutamide.

24. The composition according to claim 10, wherein said sulfonylurea is one of the following: glycazide, glipizide, glyburide, or glimeperide.

25. A method for improving glucose metabolism, comprising treating a patient for at least about a thirty day period by administering a pharmaceutical composition comprising synergistic effective amounts of an anti-diabetic agent other than insulin, a bioavailable source of chromium, and a bioavailable source of vanadium, wherein said anti-diabetic agent is a sulfonylurea, and wherein said components of said composition synergistically reduce the HbA1c level of said patient by at least about 10% after such treatment as compared to treatment with said anti-diabetic agent alone.

26. The method of claim 25, wherein said bioavailable source of chromium comprises no less than about 200 micrograms elemental chromium when said composition is administered on a daily basis.

27. The method of claim 25, wherein said bioavailable source of chromium comprises no less than about 5 micrograms of elemental chromium when said composition is administered on a daily basis.

28. The composition of claim 25, wherein said bioavailable source of chromium comprises one or more of chromium picolinate or chromium polynicotinate.

29. The method of claim 25, wherein said bioavailable source of vanadium comprises at least about 10 mg elemental vanadium when said composition is administered on a daily basis.

30. The method of claim 25, wherein said bioavailable source of vanadium is vanadyl sulfate.

31. The method of claim 25, wherein said amount of said bioavailable source of vanadium comprises no less than 5 mg of elemental vanadium when said composition is administered on a daily basis.

32. The method according to claim 25, wherein said sulfonylurea is one of the following: glycazide, glipizide, glyburide, or glimeperide.

33. The method according to claim 25, wherein said sulfonylurea is one of the following: acetohexamide, chlorpropamide, tolazimide, or tolbutamide.

34. The method according to claim 25, wherein said sulfonylurea is glyburide.

35. The method according to claim 25, wherein said sulfonylurea is glipizide.

36. The method of claim 25, wherein said pharmaceutical composition further comprises a physiologically acceptable carrier.

37. The method of claim 25, wherein said method further comprises monitoring said subject's HbA1c levels.

38. The method of claim 25, wherein said reduction in said Hb1Ac level is at least about 50%.

* * * * *